(12) United States Patent
Tronchet

(10) Patent No.: US 6,911,450 B1
(45) Date of Patent: Jun. 28, 2005

(54) PYRIMIDINE ACYCLONUCLEOSIDE DERIVATIVES, PREPARATION METHOD AND USE THEREOF

(75) Inventor: Jean M. J. Tronchet, Grilly (FR)

(73) Assignees: Universite de Geneve (CH); Mayoly Spindler (FR)

( * ) Notice: Subject to any disclaimer, the term of this patent is extended or adjusted under 35 U.S.C. 154(b) by 0 days.

(21) Appl. No.: 10/470,564

(22) PCT Filed: Jan. 25, 2002

(86) PCT No.: PCT/EP02/00839

§ 371 (c)(1),
(2), (4) Date: Jul. 29, 2003

(87) PCT Pub. No.: WO02/060880

PCT Pub. Date: Aug. 8, 2002

(30) Foreign Application Priority Data

Jan. 29, 2001 (FR) .............................. 01 01165
Jun. 19, 2001 (FR) .............................. 01 08052

(51) Int. Cl.$^7$ ..................... C07D 239/54; A61K 31/505
(52) U.S. Cl. ....................... 514/274; 544/311; 544/312
(58) Field of Search ................................ 544/311, 312; 514/274

(56) References Cited

FOREIGN PATENT DOCUMENTS

EP        0 420 763 A     4/1991
EP        0 631 783 A     1/1995

OTHER PUBLICATIONS

Tronchet et al., Antiviral Nucleoside-N-Hydroxyureas and Carbamates, Carbohydrate Letters, vol. 2, pp. 313-320, 1997.*
HIV Infection and AIDS: An Overview, National Institute of Allergy and Infectious Diseases, Oct. 2003.*
Douglas, Jr., Introduction to Viral Diseases, Cecil Textbook of Medicine, 20$^{th}$ Edition, vol. 2, pp. 1739-1747, 1996.*
Beers et al., Viral Diseases [General], The Merck Manual of Diagnosis and Therapy, 1999. http://www.merck.com/mrk-shared/mmanual/section13/chapter162/162a.jsp.*
Database Chemabs 'Online! Chemical Abstracts Service, Columbus, Ohio, US; Tronchet, Jean M. J. et al.: "Antiviral nucleoside N-hydroxyureas and carbamates" retrieved from STN Database accession no. 127:346601; XP002172470 * abrege; compose RN:198208-92-3 * & Carbohydr. Lett. (1997), 2(5), 313-320.
Pontikis, Renee et al: "Synthesis and Anti-HIV Activity of Novel N-1 Side Chain-Modified Analogs of 1-'(2-Hydroxyethoxy) methyl!-6-(phenylthio) thymine (HEPT)" J. Med. Chem. (1997), 40(12), 1845-1854, XP002172467.
Tronchet JMJ Grigorov M Dolatshahi N Moriaud F Weber J: "A QSAR study confirming the heterogeneity of the HEPT derivative series regarding their interaction with HIV reverse transcriptase" European Journal of Medicinal Chemistry. Chimica Therapeutica, FR, Editions Scientifique Elsevir, Paris, vol. 32, No. 4, 1997, pp. 279-299, XP004086652 ISSN: 0223-5234.
Luco Juan M. et al.: "QSAR Based on Multiple Linear Regression and PLS Methods for the Anti-HIV Activity of a Large Group of HEPT Derivatives", J. Chem. Inf. Comput. Sci. (1997), 37(2), 392-401, XP002172468.
Jalali-Heravi, M. et al: "Use of Artificial Neural Networks in a QSAR Study of Anti-HIV Activity for a Large Group of HEPT Derivatives" J. Chem. Inf. Comput. Sci. (2000), 40(1), 147-154, XP002172469.

* cited by examiner

*Primary Examiner*—Deepak Rao
(74) *Attorney, Agent, or Firm*—Harness, Dickey & Pierce, P.L.C.

(57) ABSTRACT

The invention relates to a compound having general formula (I): wherein n is equal to 3; $R^1$ is an ethyl or isopropyl group; each of the $R^2$ groups is independently of each other a hydrogen atom, a $C_1$-$C_3$ alkyl group or a halogen atom; one of the $R^3$ and $R^4$ groups represents a hydrogen atom while the other of the $R^3$ and $R^4$ groups represents an OH or $OR^5$ group, where $R^5$ can be a $C_2$-$C_7$ acyl group, an alkyl($C_1$-$C_6$) animo-carbonyl group, an aralkyl($C_1$-$C_6$)aminocarbonyl optionally substituted on the aryl, an arylcarbonyl group optionally substituted or a heteroarylaminocarbonyl group. Said compound is particularly suitable as an antiviral agent and especially as an anti-HIV-1 agent.

15 Claims, 1 Drawing Sheet

FIGURE
Antivirograms of three acyclonucleosides carried out on two distinct viral markers
Reverse transcriptase and P24 on HIV-1 lai
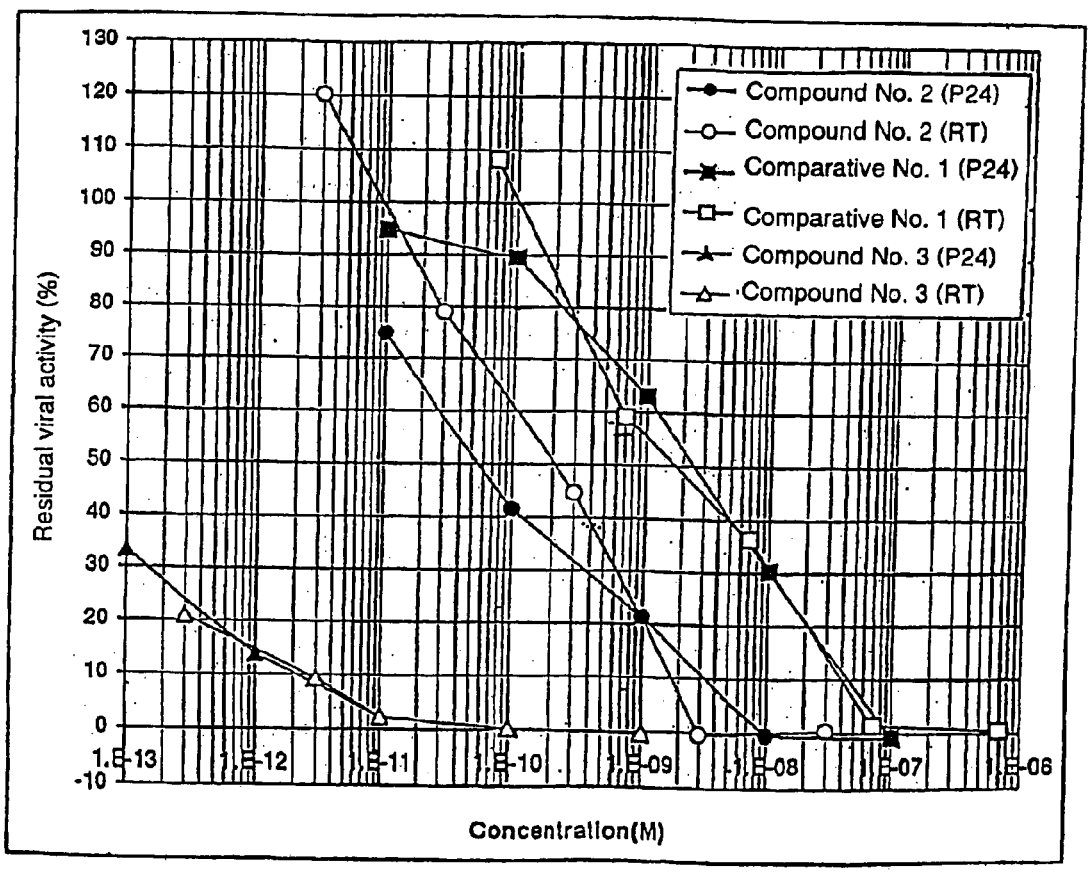

PYRIMIDINE ACYCLONUCLEOSIDE DERIVATIVES, PREPARATION METHOD AND USE THEREOF

TECHNICAL FIELD

The present invention relates to pyrimidine acyclonucleoside derivatives which are active as non-nucleosidic inhibitors of the reverse transcriptase of HIV-1, their preparation process and their use.

PRIOR ART

The current tendency in the treatment of AIDS calls for polytherapies which no longer include antiproteases whose side effects are awkward and whose mode of administering is constraining for the patient.

The recommended polytherapies therefore comprises one or two nucleosidic inhibitors which are associated with one or two non-nucleosidic inhibitors. [G. J. Moyle, *Infect. Med.* 17(6) 412–455 (2000)].

It is therefore important to develop new allosteric inhibitors of the reverse transcriptase provided with a high specific activity and a low toxicity.

Allosteric inhibitors of the reverse transcriptase having an acyclonucleoside structure are disclosed for example in the patent applications EP-A-0 449 726, WO-A-97/43266, WO-A-97/30979, WO-A-96/16675, WO-A-95/18109, EP-A-0 631 783, EP-A-0 420 763, the most known example being the EMIVIRINE having the following Formula A:

(A)

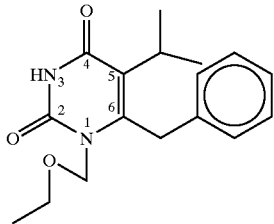

These allosteric inhibitors of the reverse transcriptase having an acyclonucleoside structure act at nanomolar concentrations and they have the disadvantage of very quickly selecting resistant mutants.

On the other hand, it has been shown by J. M. J. Tronchet, M. Zsely, M. Iznaden, F. Barbalat-Rey, M. Geoffroy & G. Bernardinelli, *Carbohydr. Lett.* 2, 101–108 (1996) in relation to the compound of the following Formula B:

(B)

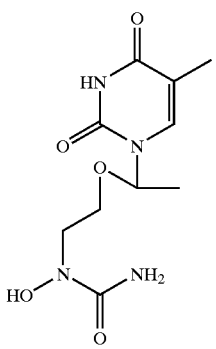

that a N-hydroxyureido residue attached at ω on the radical held by N-1 of a thymine behaves like a "pseudonucleobase" contracting in the crystal two hydrogen bonds (by its $CONH_2$ group) with the nucleobase of another molecule while the N—OH group functions as a donor of a hydrogen bond with respect to the oxygen atom of an alcohol.

The N-hydroxyureido group could thus constitute an interesting candidate for contracting new bonds with the allosteric site of the reverse transcriptase and optionally outside thereof with nucleobases of nucleic acids "treated" by the enzyme.

Further, from the point of view of the cytotoxicity of the products, one might have thought that the N-hydroxyureido group might be a good candidate because a structure-activity study of acyclonucleosides active against the HIV-1 had shown that a hydrophilic group attached at N-1 on the nucleobase should decrease the cytotoxicity of the compound [J. M. J. Tronchet, M. Grigorov, N. Dolatshahi, F. Moriaud & J. Weber, *Eur. J. Med. Chem.*, 32, 279–299 (1997)].

Thus, by introducing a N-hydroxyureido group at the ω position of the chain attached at N-1 of a pyrimidine substituted at C-4 and C-5, one could hope to improve the anti-HIV-1 activity of the already known analogue products.

However, the N-hydroxyureido group was not found to be sufficient for ensuring an activity since the first compound prepared, namely the compound having the above Formula B was found to be totally inactive against HIV-1 and the second compound prepared, namely the compound having the following Formula C [J. M. J. Tronchet, M. Iznaden, & N. Laroze, *Carbohydr. Lett.* 2, 313–320 (1997)] was found to be only very moderately active ($IC_{50}$ 70 nM).

(C)

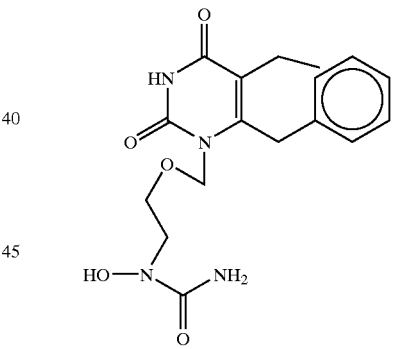

On the basis of these facts, the present inventors have continued their research and have surprisingly found that by lengthening the chain situated between the nucleobase and the N-hydroxyureido group by one carbon atom to lengthen a chain having two carbon atoms to a chain having thee carbon atoms, one could obtain an acyclonucleoside that is non-toxic and is active against HIV-1 at concentrations much lower than the ones reached until now with already known analogue products, while the same homologation made on the analogue of the compound of the Formula C bearing a hydroxyl group instead of the N-hydroxyureido group [cf. N. Laroze, Universite de Genève, Thèse No. 3212 (2000)] decreased perceptibly the activity.

The present invention has been achieved on the basis of these results.

BACKGROUND OF THE INVENTION

One object of the present invention is a compound of the following general Formula I:

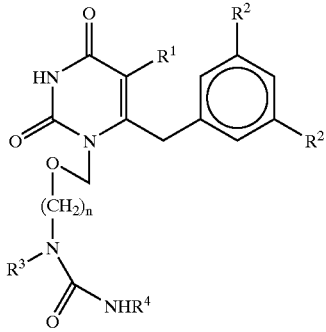

wherein:

n is equal to 3;

$R^1$ represents an ethyl group or an isopropyl group;

each of the $R^2$ groups represents independently of each other a hydrogen atom, a $C_1$–$C_3$ alkyl group or a halogen atom;

one of the $R^3$ and $R^4$ groups represents a hydrogen atom while the other of the $R^3$ and $R^4$ groups represents an —OH or —$OR^5$ group, where $R^5$ may be a $C_2$–$C_7$ acyl group, a $C_1$–$C_6$ alkylaminocarbonyl group, an ar($C_1$–$C_6$)alkylaminocarbonyl group optionally substituted on the aryl, an arylcarbonyl group optionally substituted or a heteroarylaminocarbonyl group, or a pharmaceutically acceptable salt thereof.

Further objects of the present invention are:

a compound of the Formula I as defined above for use as a medicament;

a compound of the Formula I as defined above for use as an antiviral agent, especially as an anti-HIV-1 agent;

a process for the preparation of a compound of the Formula I as defined above;

a pharmaceutical composition containing, as an active ingredient, at least one compound of the Formula I as defined above;

a pharmaceutical composition containing an amount effective as an antiviral of a compound of the Formula I as defined above; and the use of a compound of the Formula I as defined above for the manufacture of a anti-HIV medicament;

it being understood that the term "compound of the Formula I as defined above" also covers a pharmaceutically acceptable salt thereof.

DESCRIPTION OF THE FIGURE

The FIGURE represents antivirograms of three acyclonucleosides carried out on two antiviral markers, namely the reverse transcriptase and P24, to evaluate the antiretroviral activity of these three acyclonucleosides on HIV-1 lai.

DETAILED DESCRIPTION OF THE INVENTION

The compound of the present invention is represented by the following general Formula I:

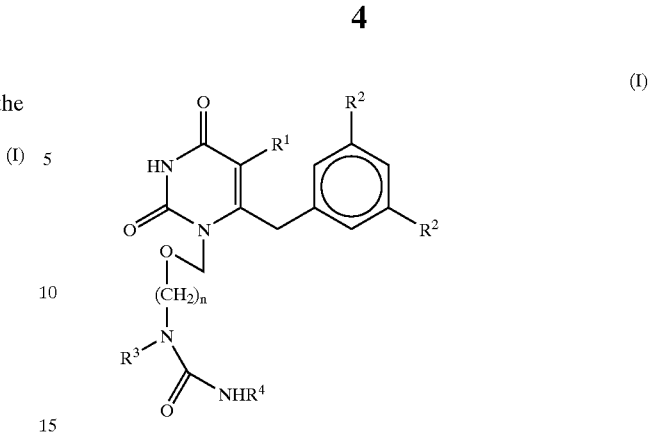

wherein n is equal to 3.

The $R^1$ group may be either an ethyl group or an isopropyl group, but preferably the $R^1$ group is an isopropyl group.

The R2 groups may be each independently of each other a hydrogen atom, a C1–C3 alkyl group, for example a methyl, an ethyl, a n-propyl or an isopropyl, or a halogen atom, for example a chlorine, a bromine, a iodine or a fluorine.

Preferably, the $R^2$ groups are identical and they represent each a methyl group.

One of the $R^3$ and $R^4$ groups represents a hydrogen atom while the other of the $R^3$ and $R^4$ groups represents a —OH group or a —$OR^5$ group, where $R^5$ is a protecting group of the hydroxy group.

Thus, when the $R^3$ group is a —OH group or a —$OR^5$ group, the $R^4$ group is a hydrogen atom; and when the $R^3$ group is a hydrogen atom, the $R^4$ group is a —OH group or a —$OR^5$ group.

However, it is preferable that the $R^3$ group be a —OH group or a —$OR^5$ group and that the $R^4$ group be a hydrogen atom.

The $R^5$ group must be selected from the hydroxy protecting groups which may be easily released in a biological medium and which are non-toxic.

The $R^5$ group is thus selected from a $C_2$–$C_7$ acyl group, a $C_1$–$C_6$ alkylaminocarbonyl group, an ar($C_1$–$C_6$)alkylaminocarbonyl group optionally substituted on the aryl, an arylcarbonyl group optionally substituted or a heteroarylaminocarbonyl group, it being understood that the acyl group and the alkyl group of the $C_1$–$C_6$ alkylaminocarbonyl and ar($C_1$–$C_6$)alkylaminocarbonyl groups may be branched or not.

Examples of the $C_2$–$C_7$ acyl group include an acetyl group, a propionyl group, a butyryl group or a pivaloyl group, without being limited to these.

Examples of the $C_1$–$C_6$ alkylaminocarbonyl group include a methylaminocarbonyl group, an ethylaminocarbonyl group, a propylaminocarbonyl group, a isopropylaminocarbonyl group, a butylaminocarbonyl group, a pentylaminocarbonyl group or a hexylaminocarbonyl group, without being limited to these.

Examples of the ar($C_1$–$C_6$)alkylaminocarbonyl group optionally substituted on the aryl include a benzylaminocarbonyl group, a phenethylaminocarbonyl group, a phenyl-3-propylaminocarbonyl group, a phenyl-4-butylaminocarbonyl group, a phenyl-5-pentylaminocarbonyl group or a phenyl-6-hexylaminocarbonyl group, as well as the above ar($C_1$–$C_6$)alkylaminocarbonyl groups wherein the aryl holds 1 or 2 substituants selected from halogens, for example a chorine, a bromine, a fluorine or a iodine, $C_1$–$C_3$ alkyl groups, for example a methyl, an ethyl, a propyl or an isopropyl and the $C_1$–$C_3$ alkoxy groups, for example a methoxy, an ethoxy, a propoxy or an isopropoxy, without being limited to these.

Examples of the arylcarbonyl group optionally substituted include a benzoyl group, a p-chlorobenzoyl group, a p-methoxybenzoyl group or a p-nitrobenzoyl group, without being limited to these.

Examples of the heteroarylaminocarbonyl group include an isoxazol-3-ylaminocarbonyl group, an isoxazol-4-ylaminocarbonyl group, an isoxazol-5-ylaminocarbonyl group, a pyridin-2-ylaminocarbonyl group or a pyridine-3-ylaminocarbonyl group, without being limited to these.

These compounds of Formula I of the present invention may be in the form of conventional pharmaceutically acceptable salts thereof.

The compounds of the present invention may be prepared according to the following Reaction Schemes wherein n, $R^1$, $R^2$, $R^3$, $R^4$ and $R^5$ have the same meanings as those defined above.

The following Reaction Scheme 1 shows the steps of the process for the preparation of the compound of Formula I of the present invention wherein $R^3$ is a —OH group or a —$OR^5$ group and $R^4$ is a hydrogen atom:

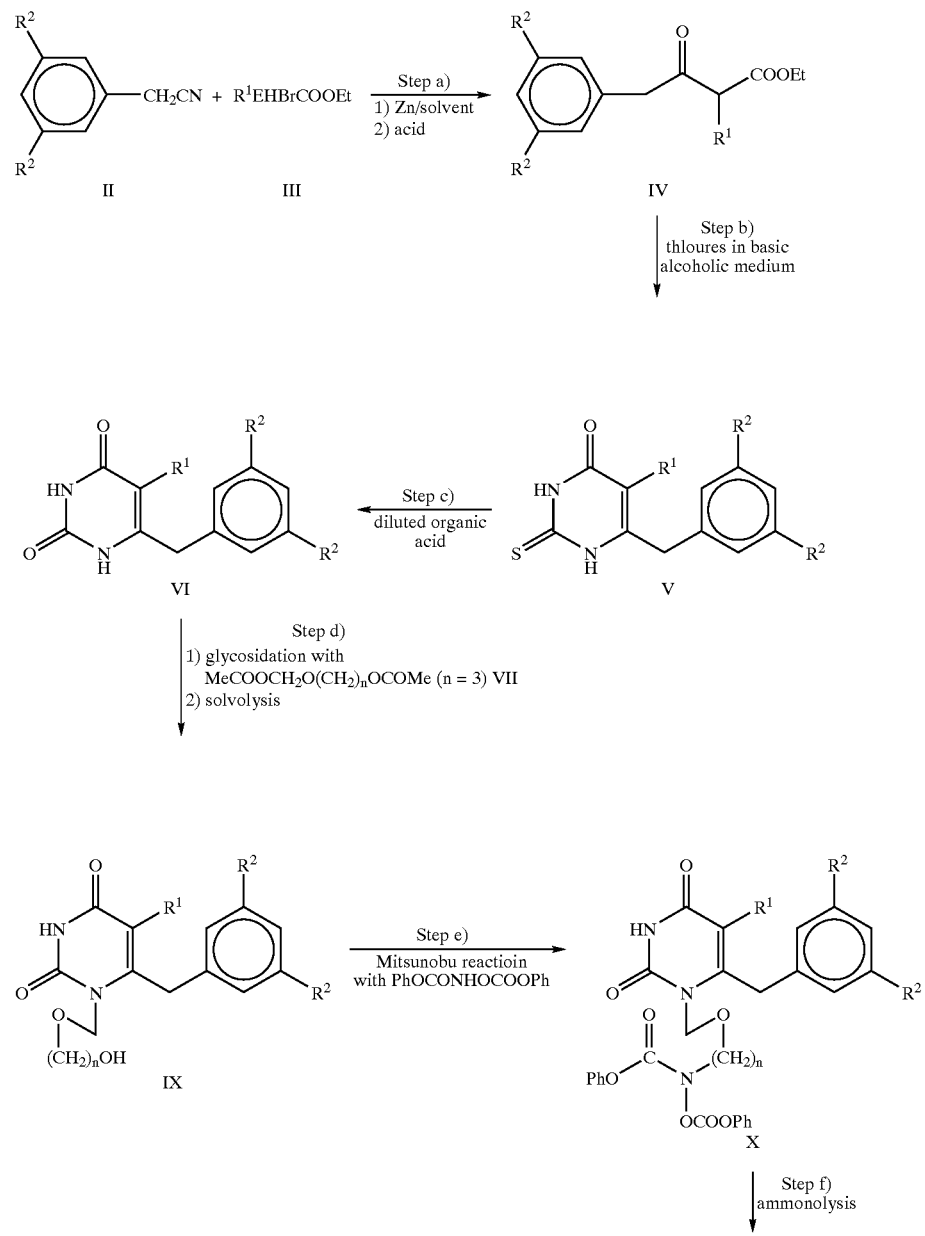

Reaction Scheme 1

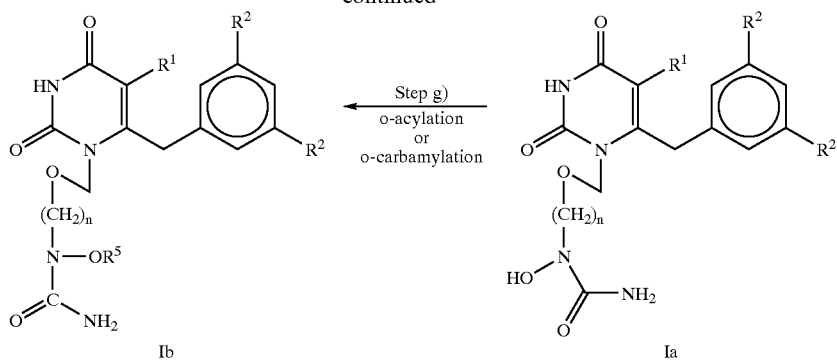

The nucleobases represented by the above Formulae V and VI are known and they are usually prepared by electrophilic substitution [cf., for example Y. S. Lee & Y. H. Kim, *Synth. Commun.* 29(9) 1503–17 (1999)].

However, in the process of the present invention, the pyrimidine ring of the modified nucleobases of the Formulae V and VI has been constructed by condensation according to the principle of the technique disclosed in S. M. Hannick & Y. Kishi, *J. Org. Chem.*, 48, 3833–3835 (1983), thus allowing a wide variety of bases to be obtained differing by the nature of the $R^1$ and $R^2$ groups.

Thus, the first step of the process, designed as step a), consists of reacting a phenylethanenitrile of the Formula II with a compound of the Formula III, in the presence of Zn in an appropriate solvent, for example an ether such as tetrahydrofuran, at an appropriate temperature, for example the reflux temperature, and then to treat the obtained mixture with an acid, for example hydrochloric acid, to obtain the compound of the Formula IV.

Then, in a step b), the compound of the Formula IV is reacted with thiourea in a basic alcoholic medium, for example in a sodium/ethanol medium (Na/EtOH), at an appropriate temperature, for example at the reflux temperature, for obtaining the thiouracil of the Formula V.

The thiouracil of the Formula V is then converted during a step c) into an uracil of the Formula VI by treatment with an appropriate diluted organic acid, for example 10% chloroacetic acid.

The fixation of the chain at $N^1$ of the nucleobase of the Formula VI is carried out in a step d) by a conventional glycosidation reaction with a compound of the Formula VII wherein n is equal to 3, for example in the presence of hexamethyldisilazane (HMDS), chlorotrimethylsilane (TMSCl) and tin tetrachloride ($SnCl_4$) followed by solvolysis of the obtained ester, for example in a methanol/triethylamine medium (MeOH/$Et_3$N), to give the alcohol of the Formula IX.

The alcohol of the Formula IX is then subjected to a Mitsunobu reaction for substituting its —OH group by a nitrogen group which will give the N-hydroxyureido group.

Thus, the treatment of the alcohol of the Formula IX in the conditions of a conventional Mitsunobu reaction by using N,O-bis(phenoxycarbonyl)hydroxylamine as a nucleophile (step e) gives the compound of the Formula X which, after conventional ammonolysis (step f), for example with ammonia or an amide anion in an appropriate solvent, gives the compound of the Formula Ia of the present invention which holds a terminal $N^1$-hydroxyureido group, namely a compound of the present invention of the Formula I wherein $R^3$ represents a —OH group and $R^4$ represents a hydrogen atom.

Then, the compound of the Formula Ia may be converted by a O-acylation or O-carbamylation reaction (step g) into a compound of the present invention of the Formula Ib, namely a compound of the present invention of the Formula I wherein $R^3$ represents a —$OR^5$ group and $R^4$ represents a hydrogen atom, as follows.

The compound of the Formula Ia of the present invention may be subjected to a conventional O-acylation reaction, for example with a conventional acylating agent of the general formula X—CO—$R^6$ (where $R^6$ is a $C_1$–$C_6$ alkyl group which may be branched or not, or an aryl group optionally substituted, X being able to be for example a halogen atom or a $R^6$COO— group, without X being limited to these), to give the monoacylated compound of the Formula Ib of the present invention wherein $R^5$ is a $C_2$–$C_7$ acyl group or an arylcarbonyl group optionally substituted, more lipophilic than its precursor Ia and wherein the N—OH group is protected against oxidation.

The compound of the Formula Ia of the present invention may be also subjected to a conventional O-carbamylation reaction, for example with a conventional carbamylating agent of the general formula X—CO—NH—$R^7$ (where $R^7$ is a $C_1$–$C_6$ alkyl group which may be branched or not, an ar($C_1$–$C_6$)alkyl group optionally substituted on the aryl and whose alkyl group may be branched or not, or a heteroaryl group, X being able to be for example a halogen atom, without X being limited to these), to give the compound of the present invention of the Formula Ib in which $R^5$ is a $C_1$–$C_6$ alkylaminocarbonyl group, an ar($C_1$–$C_6$) alkylaminocarbonyl group optionally substituted on the aryl, or a heteroarylaminocarbonyl group, more lipophilic than its precursor Ia and in which the N—OH group is protected against oxidation.

For obtaining a compound of the present invention of the Formula I in which $R^3$ is a hydrogen atom and $R^4$ is a —OH group or a —$OR^5$ group, one will refer to the following Reaction Scheme 2:

Reaction Scheme 2

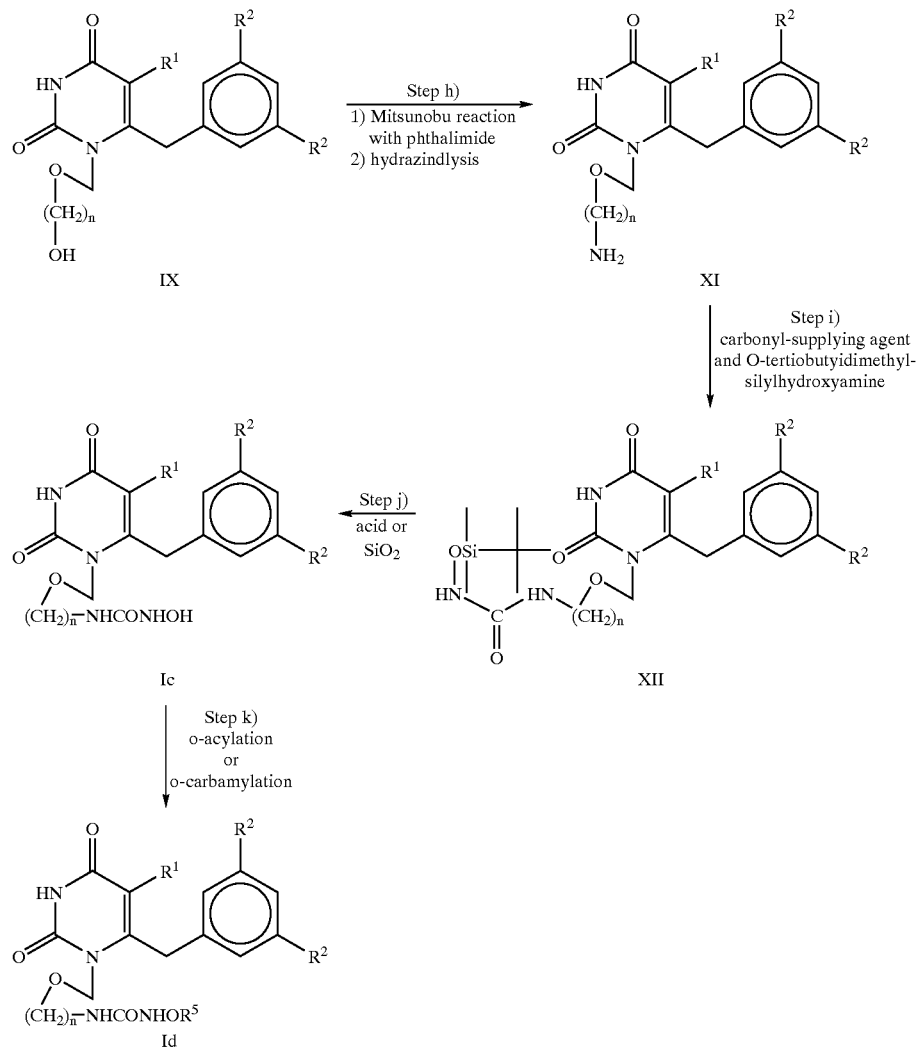

The alcohol of the Formula IX obtained as in steps a) to d) disclosed above in reference to the Reaction Scheme 1, is subjected, in a step h), to a conventional Mitsunobu reaction by using phthalimide as the nucleophile, followed by a conventional hydrazinolysis to give the amine of the Formula XI.

Then, in a step i), this amine of the Formula XI is treated in a conventional manner by a carbonyl-supplying agent, for example carbonyldiimidazole or phosgene, and the O-tertiobutyldimethylsilylhydroxylamine gives the compound of the Formula XII.

This compound of the Formula XII is then subjected to a de-O-silylation reaction (step j), for example in an acidic medium or in the presence of $SiO_2$, to give the compound of the present invention of the Formula Ic bearing a terminal $N^3$-hydroxyureido group, namely the compound of the present invention of the Formula I in which $R^3$ is a hydrogen atom and $R^4$ is a —OH group.

Then, the compound of the Formula Ic of the present invention may be converted by a O-acylation or O-carbamylation reaction (step k) into a compound of the present invention of the Formula Id, namely a compound of the present invention of the Formula I in which $R^3$ represents a hydrogen atom and $R^4$ represents a —$OR^5$ group, as follows.

The compound of the Formula Ic of the present invention may be subjected to a conventional O-acylation reaction, for example with a conventional acylating agent of the general formula X—CO—$R^6$ (where $R^6$ is a $C_1$–$C_6$ alkyl group branched or not, or an aryl group optionally substituted, X being able to be for example a halogen atom or a $R^6$COO— group, without that X being limited to these), to give the monoacylated compound of the Formula Id of the present invention in which $R^5$ is a $C_2$–$C_7$ acyl group or an arylcarbonyl group optionally substituted.

The compound of the Formula Ic of the present invention may be also subjected to a conventional O-carbamylation reaction, for example with a conventional carbamylating agent of the general formula X—CO—NH—$R^7$ (where $R^7$ is a $C_1$–$C_6$ alkyl group, branched or not, an ar($C_1$–$C_6$) alkyl group optionally substituted on the aryl and whose the alkyl group may be branched or not, or a heteroaryl group, X being able to be for example a halogen, without X being limited to these), to give the compound of the present invention of the Formula Id in which $R^5$ is a $C_1$–$C_6$ alkylaminocarbonyl group, an ar($C_1$–$C_6$) alkylaminocarbonyl group optionally substituted on the aryl, or a heteroarylaminocarbonyl group, more lipophilic than its precursor Ic and in which the N—OH group is protected against oxidation.

The compounds of the present invention may be further converted in a conventional manner into pharmaceutically acceptable salts thereof.

In order to demonstrate the efficacy of the compounds of the present invention as antiviral agents, and especially as anti-HIV-1 agents, in vitro tests have been carried out according to the following principle and working method.

Principle

The object of the screening is to evaluate the antiretroviral activity of the compounds of the present invention and of the Comparative Compounds on the HIV-1 lai strain cultivated on peripheral blood mononucleated cells (PBMC).

For this purpose, the test compounds were incubated for seven days (duration of the anti-HIV test) with the PBMC in exponential phase of growth.

The ability of the compounds to inhibit the viral replication was then measured in the culture supernatants either by an assay of the "Reverse Transcriptase" (RT) activity with the kit RetroSys TR (INNOVAGEN) or by an assay of the protein P24 with the kit Innotest HIV Antigen mAb Screening (IMMUNOGENETICS).

The concentrations of the test compound causing 50 and 90% inhibition of the viral replication were determined. It concerns inhibition concentrations $IC_{50}$ and $IC_{90}$, respectively.

Concurrently to the screening, and in the same conditions, cytotoxicity assays of the test compounds were carried out.

This assay was revealed by MTT (3-[4,5-dimethylthiazol-2-yl]-2,5-diphenyltetrazolium bromide) after seven days of culture [J. G. Park and col., *Cancer Res.* 47(22), 5875–5879 (1987)].

This assay has allowed to determine the concentration of the product causing a diminution of 50% of the growth and the viability of PBMC ($CC_{50}$).

The therapeutical index (TI) of the compound was calculated as follows: $TI_{50} = (CC_{50}/IC_{50})$.

Working Method

The PBMC were isolated as described in Ulmer and col., *Immunobiology*, 166(3), 238–250 (1984) from a healthy donor by a Ficoll gradient (Nicomed Pharma AS).

The PBMC were activated with phytohemagglutinine for three days and then cultivated in a 96-well plate, in a base medium (RPMI) supplemented with recombinant human Interleukin-2.

Throughout the culture, the cells were maintained at 37° C., in an atmosphere saturated in humidity, and under 5% $CO_2$.

The PBMC were pre-treated for one hour in the presence of the test compounds at various concentrations, and then infected with 100 $TCID_{50}$ of HIV-1-Lai [S. Wain-Hobson and col., Science 17, 252 (5008): 961–965 (1991)].

Three days after the infection with HIV-1, the half of the culture medium was changed and, at the day 7, the supernatants were taken and frozen at −20° C.

Then, the viral replication was measured:

a) by assaying the "Reverse Transcriptase" (RT) activity in the culture supernatants by means of the kit RetroSys (Innovagen).

The RT contained in the supernatant synthesizes, in the presence of bromodeoxyuridine triphosphate (BrdUTP), a complementary strand DNA to a matrix immobilized on the bottom of the wells of a 96-well plate. The incorporation of BrdU is quantified by the fixation of an antibody anti-BrdU conjugated to the alkaline phosphatase. The activity of the attached alkaline phosphatase, measured by colorimetry, is proportional to the RT activity in the culture supernatant.

b) by assaying the protein P24 in the culture supernatants by means of the kit Innotest HIV Antigen mAb Screening (IMMUNOGENETICS).

The P24 of supernatants binds to polyclonal antibodies anti-HIV immobilized at the bottom of the wells of a 96-well plate. A secondary antibody biotinyl anti-P24 binds to the P24. Then, the biotin binds the streptavidine whose activity, measured by colorimetry, is proportional to the amount of P24 present in the culture supernatant.

The results described below are the results of at least two experiments which are distinct and carried out in triplicate.

Compounds of the Invention which have been Tested:

Compound 1: 1-(3-$N^3$-hydroxyureidopropyloxymethyl)-6-(3,5-dimethylbenzyl)-5-ethyl-uracil Compound 2: 1-(3-N1-hydroxyureidopropyloxymethyl)-6-(3,5-dimethylbenzyl)-5-ethyl-uracil Compound 3: 1-(3-$N^1$-hydroxyureidopropyloxymethyl)-6-(3,5-dimethylbenzyl)-5-isopropyluracil Compound 4: 1-(3-$N^1$-acetoxyureidopropyloxymethyl)-6-(3,5-dimethylbenzyl)-5-isopropyluracile.

Compound 5: 1-(3-$N^1$-pivaloyloxyureidopropyloxymethyl)-6-(3,5-dimethylbenzyl)-5-isopropyluracil.

Comparative Compound which have been Tested:

Comparative 1: 1-(2-$N^1$-hydroxyureidoethyloxymethyl)-6-(3,5-dimethylbenzyl)-5-ethyluracil Comparative 2: 1-(4-$N^1$-hydroxyureidobutyloxymethyl)-6-(3,5-dimethylbenzyl)-5-ethyluracil Comparative 3: 1-(2-$N^1$-hydroxyureidoethyloxymethyl)-6-benzyl-5-ethyluracile (Compound of the Formula C)

Comparative 4: 1-ethyloxymethyl-6-benzyl-5-isopropyluracil (Compound of the Formula A)

The Compounds Nos. 1, 2, 3, 4 and 5 of the present invention and the Comparative Compounds Nos 1, 2 and 3 which have been tested have been synthesized as indicated in the Examples, and the Comparative Compound No. 4 has been synthesized as disclosed in the literature [M. Baba, H. Tanaka, T. Miyasaka, S. Yuseda, M. Ubasawa, R. T. Walker & E. De Clerq, *Nucleosides Nucleotides*, 14, 575–583 (1995)].

Results of the Tests

The results of the tests resulting from the assays of the "Reverse Transcriptase" activity and of the protein P24 with the Compounds Nos. 2 and 3 of the present invention and the Comparative Compound No. 1 are shown on the antivirograms represented on the Figure.

These results show clearly that the test compounds inhibit in a parallel manner the production of two distinct viral markers, namely the reverse transcriptase and the protein P24.

Therefore, these compounds are inhibitors of the replication of the HIV-1 virus.

The results of the tests resulting from the assay of the "Reverse Transcriptase" (RT) activity are indicated in Table 1 below which shows the inhibition concentrations at 50% ($IC_{50}$) and at 90% ($IC_{90}$) against the HIV-Lai in nM, the cytotoxic concentrations at 50% ($CC_{50}$) in nM and the therapeutical index $TI_{50}$ ($CC_{50}/IC_{50}$) of the Compounds Nos. 1, 2, 3, 4 and 5 of the present invention and of the Comparative Compounds No. 1, 2, 3 and 4.

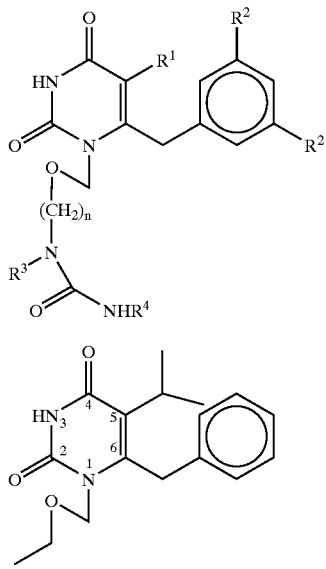

Furthermore, during tests carried out on one of the compounds of the present invention, namely the Compound No. 2, it was shown that this compound exhibited a synergy with AZT (3'-azido-3'-desoxythymidine), ddI (2',3'-didesoxyinosine) and ddC (2',3'-didesoxycytidine), thus implying that the compound of the present invention in general may be advantageously used with at least AZT, ddI and/or ddC.

Thus, the compound of the present invention or a pharmaceutically acceptable salt thereof may be used as an active ingredient in a pharmaceutical composition, and it may be used either alone, or in mixture with other active ingredients, especially in a pharmaceutical composition provided to be used as a medicament as a part of a polytherapy.

The present invention provides thus also a pharmaceutical composition containing as an active ingredient at least one compound of the present invention or a pharmaceutically acceptable salt thereof.

The amount of the compound of the present invention or of its pharmaceutically acceptable salt contained in the composition will depend especially on the weight, the age and the condition of the patient as well as on the efficacy of the compound.

The pharmaceutical composition of the present invention may be in a form orally or systemically administrable, and

TABLE 1

| | $R^1$ | $R^2$ | n | $R^3$ | $R^4$ | $IC_{50}$ (nM) | $IC_{90}$ (nM) | $CC_{50}$ (nM) | $TI_{50}$ |
|---|---|---|---|---|---|---|---|---|---|
| Compounds of the invention | | | | | | | | | |
| 1 | Et | Me | 3 | H | OH | 2.3 | 9 | $2.6 \times 10^5$ | $1.13 \times 10^5$ |
| 2 | Et | Met | 3 | OH | H | 0.24 | 1.7 | $>3 \times 10^5$ | $>10^6$ |
| 3 | iPr | Me | 3 | OH | H | $3 \times 10^{-5}$ | $3.9\ 10^{-3}$ | $2.2 \times 10^5$ | $7 \times 10^9$ |
| 4 | iPr | Me | 3 | OAc | H | 0.03 | 0.6 | $3 \times 10^4$ | $10^6$ |
| 5 | iPr | Me | 3 | OOCCMe$_3$ | H | $1 \times 10^{-6}$ | | $6.5 \times 10^4$ | $6.5 \times 10^{10}$ |
| Comparative Compounds | | | | | | | | | |
| Comparative 1 | Et | Me | 2 | OH | H | 0.92 | 15 | $>5 \times 10^5$ | $>1.1 \times 10^6$ |
| Comparative 2 | Et | Me | 4 | OH | H | 2.3 | 30 | $>0.5 \times 10^5$ | $>0.25 \times 10^5$ |
| Comparative 3 (Formula C) | Et | H | 2 | OH | H | 70 | | $>2.5 \times 10^5$ | $>3.5 \times 10^3$ |
| Comparative 4 (Formula A) | | | | | | 2 | | $>3 \times 10^4$ | $>1.5 \times 10^4$ |

As can be seen in Table 1, the compounds of the present invention were found to be antivirals highly active against HIV-1, in particular the Compound No. 3 having the Formula I in which $R^1$=—CHMe$_2$, $R^2$=Me, $R^3$=—OH and $R^4$=H, namely the 1-(3-N$^1$-hydroxyureidopropyloxymethyl)-6-(3,5-dimethylbenzyl)-5-isopropyluracil, for which one can observe an activity 100,000 times higher than that of its congeners or of its rivals, and more particularly the Compound No. 5 having the Formula I in which $R^1$=—CHMe$_2$, $R^2$=Me, $R^3$=—OOCCMe$_3$ and $R^4$=—H, namely the 1-(3-N$^1$-pivaloyloxyureido-propyloxymethyl)-6-(3,5-dimethylbenzyl)-5-isopropyluracil, for which one can observe the spectacular and unpredictable activity, namely an activity 1,000,000 times higher than that of its congeners or of its rivals.

The present invention provides therefore a new type of acyclonucleosides as antiviral agent, especially acting as non-nucleosidic inhibitor of the reverse transcriptase of HIV-1, which is non-toxic, and which may be active at picomolar, and even femtomolar concentrations.

it may contain any appropriate pharmaceutically acceptable carriers or excipients.

The compound of the present invention contained in the pharmaceutical composition may be advantageously a compound in which $R^3$ or $R^4$ is a —OR$^5$ group.

In this case, the compound of the present invention is a prodrug which, after administration, will be converted in the body into a compound of the present invention in which $R^3$ or $R^4$ is a —OH group.

Such a compound where $R^3$ or $R^4$ is a —OR$^5$ group will be especially able to be advantageously used in a delay formulation.

The compound of the present invention in which $R^5$ is an acyl group is particularly advantageous because it is more lipophilic than its precursor and the N—OH group is protected against oxidation. Further, it may be deacylated in the blood at rates controllable by the nature of the acyl group.

The use of branched $R^5$ groups, such as for example the pivaloyl group, is also advantageous because it allows to delay the hydrolysis of the ester group by the esterases.

Owing to the present invention, it has been possible to improve the fixation on the receptor, namely the allosteric site of the reverse transcriptase of HIV-1, this becoming apparent by a lower inhibition concentration, this implying a better selectivity, a lower preparation cost, and a lower tendency to select resistant mutants.

An other advantage of acyclonucleosides having N-hydroxyureido group of the present invention is that they are able to be detected by Electronic Paramagnetic Resonance (EPR) after oxidation into corresponding aminoxyl free radicals.

The air-oxidation, optionally promoted by a low UV irradiation, leads to a very low stationary concentration of paramagnetic species which, considering the high sensibility and the high selectivity of the EPR technique, allows the molecule to be observed in complex biological media.

Toxicity tests of Compounds No. 3 and 5 of the present invention were further carried out on bone marrow cells according to the following working method.

Bone marrow cells of Balb/c mice were cultivated at the rate of $5 \times 10^5$ cells/ml in cultures of 1 ml in RPMI 1640 medium supplemented with 1 mM glutamine, 10% fetal calf serum, penicillin and streptomycin (GIBCO, USA).

The cells were stimulated by addition of 1 ng/ml of Stem cell factor (c-kit ligand), IL3 and GM-CSF (Pharmingen, USA) in the presence of increasing concentrations of the Compounds 3 and 5 of the present invention ranging from $1 \times 10^{-12}$ to $1 \times 10^{-5}$ M.

After 5 days of culture at 37° C., 5% $CO_2$, the cells were recovered.

The proliferation was evaluated by numeration of living cells in the presence of Trypan blue.

The differentiation of the cells was evaluated by Flow Cytometry (Facs-Calibur, BECTON DICKINSON, USA) by double labeling of the cells with antibodies anti-CD38 conjugated with phycoerythrine (PE), anti-Gr1 conjugated with fluoresceine 5 (Fl), anti-Gr1-PE and anti-CD11b-Fl (Pharmingen, USA).

At all the tested concentrations, the cell proliferation was identical to the one observed in the absence of the Compound No. 3 or 5 of the present invention.

In the same way, the proportions of lymphocytes B, myelocytes, neutrophiles and macrophages induced by the cytokines were identical in the presence or in the absence of the Compound No. 3 or 5 of the present invention, whatever be the concentration.

These results show clearly that the compounds of the present invention, and in particular the Compounds 3 and 5 of the present invention have no significant toxic effects on bone marrow cells of mice and do not interfere with their in vitro differentiation, even at concentrations $1 \times 10^6$ time higher than those giving a inhibition of the replication of HIV in human lymphocytes in vitro.

The following examples are intended to illustrate the present invention. However, they cannot be considered in any case as limiting the scope of the present invention.

EXAMPLES

The starting materials, the reagents and the solvents used in the following synthesis are all available products supplied by Fluka (Buchs, Switzerland), Merck (Darmstadt, Germany), or Aldrich (Buchs, Switzerland), unless otherwise being specified.

Example 1

Synthesis of 1-(3-$N^1$-hydroxyureidopropyloxymethyl)-6-(3,5-dimethylbenzyl)-5-isopropyluracil (Compound No. 3 of the present invention) (Compound of the present invention of the Formula I, in which n=3, $R^1$ is an isopropyl group, each of $R^2$ is a methyl group, $R^3$ is a —OH group and $R^4$ is a hydrogen atom)

A. Synthesis of 6-(3,5-dimethylbenzyl)-5-isopropyluracil (Compound of the Formula VI according to the Reaction Scheme 1 in which $R^1$ is an isopropyl group and each of $R^2$ is a methyl group)

To a solution of 2-bromo-3-methylbutanoic acid (3 g, 16.5 mmol) in ethanol (200 ml), was added concentrated sulfuric acid (4 ml). After 36 h under reflux ebullition, the reaction medium, returned to ambient temperature, was neutralized with an aqueous saturated sodium carbonate solution. After distillation of the ethanol, the reaction medium was extracted with dichloromethane (100 ml). The organic phase was dried over magnesium sulfate and the solvent was evaporated to give ethyl 2-bromo-3-methylbutanoate (1.91 g, 55%).

A suspension of Zn powder (31.5 g, 0.48 mol) in tetrahydrofuran (300 ml) was boiled under reflux, and then it was added thereto a few drops of ethyl 2-bromo-3-methylbutanoate to initiate the reaction. After 45 mn under reflux and under magnetic stirring, it was added thereto 3,5-dimethylphenylethanenitrile (13.2 g, 91 mmol), and then, dropwise, the remainder of ethyl 2-bromo-3-methylbutanoate (in total 19.1 g, 91 mmol). The ebullition was maintained for 15 mn, the mixture was then cooled, and then it was added thereto tetrahydrofuran (500 ml) and a 50% aqueous potassium carbonate solution (100 ml). After 45 mn under vigorous stirring, the organic phase was separated by decantation and the aqueous phase was washed with tetrahydrofuran (2×100 ml). The collected organic phases were treated with 10% aqueous hydrochloric acid solution (300 ml) for 45 mn. After elimination of tetrahydrofuran by distillation under reduced pressure, the residue was taken again with dichloromethane (300 ml), and the organic phase was washed with a saturated sodium monohydrogenocarbonate solution (100 ml), dried over magnesium sulfate and concentrated. The distillation of the residue (134° C., $10^{-1}$ mmHg) gave ethyl 3-methyl-2-(3,5-dimethylphenylacetyl)butanoate (13.2 g, 52%).

Metal sodium (23.8 g, 1.034 mol) was reacted with anhydrous ethanol (500 ml). To the clear obtained solution, was added thiourea (54.35 g, 714 mmol) and ethyl 3-methyl-2(3,5-dimethylphenylacetyl)butanoate (13.14 g, 47.6 mol). The reaction medium was maintained under reflux for 6 h, and then was concentrated in vacuo at 40.50° C. To the obtained residue was added concentrated hydrochloric acid (100 ml) and then the solution was brought to pH 4 with acetic acid. The obtained 6-dimethylbenzyl-5-isopropyl-2-thiouracil was dissolved in an aqueous 10% chloroacetic acid solution (200 ml) and the solution was maintained under reflux for 24 h and then cooled to ambient temperature and the obtained precipitates were separated by filtration and washed with cold ethanol and then with ether, and then dried in vacuo at 40° C. to give 6-(3,5-dimethylbenzyl)-5-isopropyluracil (7 g, 54%). Melting point: 213–214° C.

B. Synthesis of 1-acetoxy-3-acetoxymethoxypropane (Compound of the formula VII according to the Reaction Scheme 1, in which n=3)

To a mixture of 1,3-dioxan (3 ml, 0.035 mmol) and acetic anhydride (3.3 ml, 0.035 mmol) at 0° C., was added a drop of concentrated sulphuric acid. The mixture was then stirred for 14 h at 20° C., added with sodium acetate (2 g) and filtrated. The residue, distilled in vacuo (120° C., 16 mmHg), gave 1-acetoxy-3-acetoxymethoxypropane (3.34 g, 50%) as a colorless oil.

¹H-NMR (200 MHz, CDCl₃): δ 1.90 (quint., 2H, J=6 Hz, CH₂—C$\underline{H_2}$—CH₂), 2.04 (s, 3H, OAc), 2.09 (s, 3H, OAc), 3.69 (t, 2H, J=6 Hz, OC$\underline{H_2}$—CH₂—CH₂—OAc), 4.14 (t, 2H, J=6 Hz, OCH₂CH₂C$\underline{H_2}$OAc), 5.22 (s, 2H, AcOC$\underline{H_2}$O). IR (KBr): $v_{max}$ 2994($v_{C-H}$), 1706 and 1682($v_{C=O}$), 1225, 1074 cm⁻¹.

C. Synthesis of 1-(3-N¹-hydroxyureidopropyloxymethyl)-6-(3,5-dimethylbenzyl)-5-isopropyluracil (Compound No. 3 of the Present Invention)

To a solution of 6-(3,5-dimethylbenzyl)-5-isopropyluracil (1.5 g, 5.5 mmol) obtained in the above step A and 1-acetoxy-3-acetoxymethoxypropane (2.1 g, 11 mmol) obtained in the above step B in ethanenitrile (60 ml), was added hexanemethyidisilazane (1.78 g, 11 mmol) and chlorotrimethylsilane (1.2 g, 11 mmol). After 15 mn at 20° C., it was added dropwise thereto a solution of tin$^{IV}$ chloride (2.87 g, 11 mmol) in ethanenitrile (15 ml). After 14 h under stirring at 20° C., it was added thereto dichloromethane (100 ml) and an aqueous saturated sodium hydrogenocarbonate solution (50 ml). The organic phase was then washed with an aqueous saturated sodium hydrogenocarbonate solution (30 ml) and then with a saturated sodium chloride solution (30 ml), and was dried over magnesium sulphate, and concentrated. The obtained residue was subjected to a flash column chromatography (petroleum ether/ethyl acetate 1:1, $R_F$=0.41) to give 1-acetoxypropyloxymethyl)-6-(3,5-dimethylbenzyl)-5-isopropyluracil (1.73 g, 75%) in the form of a viscous oil.

This acetylated derivative (1.7 g, 4.05 mmol) was dissolved in methanol (40 ml) and it was added thereto triethylamine (5 ml) and water (5 ml). After 48 h under stirring at 20° C., the reaction was completed (TLC). The reaction medium was concentrated, the remaining volatile products were eliminated by co-evaporation with toluene and the residue was subjected to a flash column chromatography (dichloromethane/methanol 99.5:0.5) to give 1-(3-hydroxypropyloxymethyl)-6-(3,5-dimethylbenzyl)-5-isopropyluracil (1.43 g, 93%).

To a solution of this alcohol (1.43 g, 3.96 mmol), N,O-(diphenoxycarbonyl)-hydroxylamine (1.2 g, 4.36 mmol) and triphenylphosphine (1.25 g, 4.76 mmol) in tetrahydrofuran (30 ml), was added dropwise at 0° C. a solution of diisopropyl azodicarboxylate (0.97 g, 4.76 mmol) in tetrahydrofuran (5 ml). The reaction medium was concentrated and subjected to a flash column chromatography (methanol/chloroform 0.3:9.7) to give 6-(3,5-dimethylbenzyl)-1-[3-(N-phenoxycarbonyl-N-phenoxycarbonyloxyamino)propyloxymethyl]-5-isopropyluracil (1.8 g, 79%) in the form of a solid.

Melting point: 59–61° C.

¹H-NMR (200 MHz, CDCl₃): δ 1.23 (d, 6H, J=6.5 Hz, CH-$\underline{Me_2}$), 2.03 (quint, 2H, J=6 Hz, CH₂—C$\underline{H_2}$—CH₂), 2.29 (s, 6H, $\underline{Me_2}$Ph), 2.82 (sept., 1H, C$\underline{H}$Me₂), 3.75 (t, 2H, OC$\underline{H_2}$—CH₂—CH₂—N), 3.95 (t, 2H, NC$\underline{H_2}$CH₂CH₂O), 4.09 (s, 2H, C$\underline{H_2}$Ar), 5.12 (s, 2H, NC$\underline{H_2}$O), 6.70 (s, 2H, H$_{ortho-benzyl}$), 6.90 (s, 1H, H$_{para-benzyl}$), 7.10–7.48 (m, 10, 2PhO), 8.1 (broad s, 1H, NH).

IR (CH₂Cl₂): $v_{max}$ 3382($v_{N-H}$), 3050–2870($v_{C-H}$), 1806, 1741, 1707 and 1682($v_{C=O}$) cm⁻¹.

Elemental Analysis for C₃₄H₃₇N₃O₈: Calculated: C, 66.33; H, 6.06; N, 6.82. Found: C, 66.33; H, 6.12; N, 6.83.

A solution of this latter compound (1.8 g, 3.13 mmol) in ammonia saturated methanol was stirred at 20° C. until the disappearance of the starting product (reaction followed by TLC). The residue was subjected to a flash column chromatography (methanol/ethyl acetate 1:9) to give the desired 1-(3-N¹-hydroxyureidopropyloxy-methyl)-6-(3,5-dimethylbenzyl)-5-isopropyluracil (0.74 g, 60%) in the form of a solid.

Melting point: 88–90° C.

¹H-NMR (200 MHz, CDCl₃): δ 1.29 (d, 6H, J=6.5 Hz, CH$\underline{Me_2}$), 1.89 (quint, 2H, J=6 Hz, CH₂—C$\underline{H_2}$—CH₂), 2.28 (s, 6H, $\underline{Me_2}$Ph), 2.88 (sept., 1H, C$\underline{H}$Me₂), 3.62 (t, 2H, OC$\underline{H_2}$—CH₂—CH₂—N), 3.68 (t, 2H, NC$\underline{H_2}$CH₂CH₂O), 4.09 (s, 2H, C$\underline{H_2}$Ar), 5.11 (s, 2H, NCH₂O), 6.70 (s, 2H, H$_{ortho-benzyl}$), 6.90 (s, 1H, H$_{para-benzyl}$), 9.00 and 9.87 (2 broad s, 3H, NH).

IR (CH₂Cl₂): $v_{max}$ 3530($v_{O-H}$), 3430, 3372 and 3190($v_{N-H}$), 3000–2850($v_{C-H}$), 1681.5($v_{C=O}$) cm⁻¹.

Elemental Analysis for C₂₁H₃₀N₄O₅.1/2H₂O: Calculated: C, 59.00; H, 7.31; N, 13.11. Found: C, 58.83; H,7.15; N, 12.82.

Example 2

Synthesis of 1-(3-N¹-acetoxyureidopropyloxymethyl)-6-(3,5-dimethylbenzyl)-5-isopropyluracil (Compound No. 4 of the Present Invention)

(Compound of the present invention of the Formula I, in which n=3, R¹ is an isopropyl group, each of R² is a methyl group, R³ is a —OR⁵ group, where R⁵ is a —CO—CH₃ group and R⁴ is a hydrogen atom).

To a solution of 1-(3-N¹-hydroxyureidopropyloxymethyl)-6-(3,5-dimethylbenzyl)-5-isopropyluracil obtained in the above Example 1-C (85 mg, 0.2 mmol) in dichloromethane (3.5 ml), was added DMAP (4-dimethylaminopyridine) (5 mg, 0.04 mmol), triethylamine (45 μl, 0.3 mmol) and acetic anhydride (25 μl, 0.24 mmol) and the mixture was stirred for 3 hours at 20° C. Then, it was added thereto dichloromethane (5 ml) and an aqueous saturated sodium hydrogenocarbonate solution (5 ml). The reaction medium was then extracted with dichloromethane (50 ml) and the organic phase was washed with water (10 ml) and then with a saturated sodium chloride solution (10 ml) and dried (sodium sulfate). The organic phase was then concentrated and subjected to a flash column chromatography on silica gel (dichloromethane/methanol 9:1) to give 70 mg (75%) of the desired 1-(3-N¹-acetoxyureidopropyloxymethyl)-6-(3,5-dimethylbenzyl)-5-isopropyluracil in the form of a solid.

Melting point: 77–79° C.

¹H-NMR (200 MHz, CDCl₃): δ 1.31 (d, 6H, J=7.0 Hz, CH$\underline{Me_2}$), 1.84 (quint, 2H, J=6.5 Hz, CH₂—C$\underline{H_2}$—CH₂), 2.22 (s, 3H, OAc), 2.31 (s, 6H, $\underline{Me_2}$Ph), 2.86 (sept., 1H, C$\underline{H}$Me₂), 3.67 (t, 2H, OC$\underline{H_2}$—CH₂—CH₂—N), 3.75 (t, 2H, NC$\underline{H_2}$CH₂CH₂O), 4.10 (s, 2H, C$\underline{H_2}$Ar), 5.10 (s, 2H, NCH₂O), 6.72 (s, 2H, H$_{ortho-benzyl}$), 6.91 (s, 1H, H$_{para-benzyl}$), 8.65 (broad s, 1H, NH).

IR (CH₂Cl₂): $v_{max}$ 3531, 3420, 3372, 3195($v_{N-H}$), 3055–2871($v_{C-H}$), 1795($v_{C=O}$ Ac), 1784, 1683($v_{C=O}$ CON) cm⁻¹.

MS (m/z (%)) 444 (2, M·⁺-NH₂), 385 (16, M·⁺-NH₂—AcO), 302 (1, BH⁺), 301 (7, B⁺), 287 (2, BH⁺-Me), 286 (B⁺-Me).

Elemental Analysis for C₂₃H₃₂N₄O₆.1/2H₂O (469.61): Calculated: C, 58.83; H, 7.08; N, 11.93. Found: C, 58.92; H, 6.98; N, 11.83.

Example 3

Synthesis of 1-(3-N$^1$-pivaloyloxyureidopropyloxymethyl)-6-(3,5-dimethylbenzyl)-5-isopropyluracil (Compound No. 5 of the Present Invention)

(Compound of the present invention of the Formula I, in which n=3, R$^1$ is an isopropyl group, each of R$^2$ is a methyl group, R$^3$ is a pivaloyloxy group (Me$_3$CCOO—) and R$^4$ is a hydrogen atom).

To a solution of 1-(3-N$^1$-hydroxyureidopropyloxymethyl)-6-(3,5-dimethylbenzyl)-5-isopropyluracil obtained in the above Example 1-C (134 mg, 0.32 mmol) in pyridine (1.5 ml) was added 46 mg (0.38 mmol) of pivaloyl chloride. After 14 h under stirring at 24° C., pyridine was eliminated by co-evaporation with toluene (2×3 ml) and the residue was taken again with dichloromethane (10 ml). The organic phase was then washed with an aqueous saturated sodium hydrogenocarbonate solution (10 ml). The aqueous phase was extracted with dichloromethane (3×10 ml) and the organic phases collected, washed with an aqueous sodium hydrogenocarbonate solution (10 ml), an aqueous saturated sodium chloride solution (10 ml), dried (sodium sulfate) gave by distillation of the solvent 180 mg of crude 1-(3-N$^1$-pivaloyloxyureidopropyloxymethyl)-6-(3,5-dimethylbenzyl)-5-isopropyluracil which was subjected to a flash column chromatography on silica gel (dichloromethane/methanol 24:1) to give 127 mg (78%) of the desired 1-(3-N$^1$-pivaloyloxyureidopropyloxymethyl)-6-(3,5-dimethylbenzyl)-5-isopropyluracil in the form of a solid.

Melting point 132–133° C.; R$_F$ 0.22 (dichloromethane/methanol 24:1). UV (MeOH) nm (ε): 210 (17500) and 268 (9420).

$^1$H-NMR (200 MHz, CDCl$_3$): δ 1.27 (d, 6H, J=6.5 Hz, CH<u>Me$_2$</u>), 1.29 (s, 9H, CMe$_3$), 1.80 (quint., 2H, J=6 Hz, CH$_2$—<u>CH$_2$</u>—CH$_2$), 2.28 (s, 6H, <u>Me$_2$</u>Ph), 2.86 (sept, 1H, <u>CH</u>Me$_2$), 3.62 (t, 2H, O<u>CH$_2$</u>CH$_2$CH$_2$N), 3.72 (t, 2H, OCH$_2$CH$_2$<u>CH$_2$</u>N), 4.08 (s, 2H, <u>CH$_2$</u>Ar), 5.09 (s, 2H, NCH$_2$O), 6.69 (s, 2H, H$_{ortho-benzyl}$), 6.89 (s, 1H, H$_{para-benzyl}$), 8.66 (s el, 1H NH).

$^{13}$C-NMR (50 MHz, CDCl$_3$): δ 20.4 (<u>Me$_2$</u>Ar), 21.3 (<u>Me$_2$</u>CH), 26.8 (NCH$_2$<u>CH$_2$</u>CH$_2$—O), 27.0 (<u>Me$_3$</u>C), 28.4 (Me$_2$<u>CH</u>), 33.3 (<u>CH$_2$</u>Ar), 38.5 (Me$_3$<u>C</u>), 46.6 (N<u>CH$_2$</u>—CH$_2$CH$_2$), 66.4 (O<u>CH$_2$</u>CH$_2$CH$_2$N), 73.1 (NCH$_2$O), 119.6 (C-5), 125.0 (C$_{ortho}$-Ar), 128.8 (C$_{para}$-Ar), 135.1 (C$_{ipso}$-Ar), 138.8 (C$_{meta}$-Ar), 148.8 (C-2), 151.8 (C-6), 158.8 (CONH$_2$), 162.3 (C-4), and 175.7 (<u>C</u>OCMe$_3$).

IR (CH$_2$Cl$_2$): ν$_{max}$ 3535 (ν$_{N-H}$), 3430 and 3386 (ν$_{NH2}$), 3052 (ν$_{C-H}$ asymetric), 1779 (ν$_{C=O}$ ester), 1705, 1684 (ν$_{C=O}$ CON) cm$^{-1}$.

MS m/z (%): 355 (4, B—CH$_2$—OCH$_2$CH$_2$CN$^+$), 301 (2, B—CH$_2$O$^+$), 285 (3, B—CH$_2^+$), 273 (13, BH$_2^+$), 272 (62, BH$^+$), 271 (5, B$^+$), 257 (100, BH$^+$-Me).

Elemental Analysis for C$_{26}$H$_{38}$N$_4$O$_6$ (502.62), 0.5 CH$_2$Cl$_2$): Calculated: C, 58.39; H, 7.21; N, 10.28. Found: C, 58.14; H, 7.20; N, 10.13.

Example 4

Synthesis of 1-(3-N$^3$-hydroxyureidopropyloxymethyl)-6-(3,5-dimethylbenzyl)-5-ethyluracil (Compound No. 1 of the Present Invention)

(Compound of the Formula I of the present invention in which n=3, R$^1$ is an ethyl group, each of R$^2$ is a methyl group, R$^3$ is a hydrogene atom and R$^4$ is a OH group)

A. Synthesis of 5-ethyl-1-(3-hydroxypropopyloxymethyl)-6-(3,6-dimethyl-benzyle) uracil (Compound of the Formula IX according to the Reaction Scheme 1 in which R$^1$ is an ethyl group and each of R$^2$ is a methyl group)

To a suspension of 5-ethyl-6-(3,5-dimethylbenzyl)uracil (645 mg, 5 mmol) (prepared as described for the preparation of 6-(3,5-dimethylbenzyl)-5-isopropyluracil in the above Example 1-A but in replacing the 2-bromo-3-methylbutanoic acid by the 2-bromobutanoic acid) and 1-acetoxy-3-acetoxymethoxypropane (prepared as described in the above Example 1-B) (950 mg, 5 mmol) in ethanenitrile (25 ml), were added hexamethyldisilazane (810 mg, 5 mmol) and chlorotrimethylsilane (545 mg, 5 mmol). After 10 minutes under stirring at 20° C., it was added dropwise thereto, in 10 minutes, a solution of tin$^{IV}$ chloride (782 mg, 2.4 mmol) in ethanenitrile (7 ml). After 14 h under stirring, it was added to the reaction medium dichloromethane (70 ml) and an aqueous saturated sodium hydrogenocarbonate solution (70 ml). The organic phase was separated by decantation and the aqueous phase was extracted with dichloromethane (3×50 ml). The collected organic phases were washed with saturated sodium hydrogenocarbonate solution (25 ml), with water (25 ml) and with an aqueous saturated sodium chloride solution (25 ml). The organic phase was dried over sodium sulfate, concentrated, and subjected to a flash column chromatography on silica gel (ethyl acetate/petroleum ether 1:1) to give 0.85 g (87%) of 5-ethyl-1-(3-acetoxypropyloxymethyl)-6-(3,5-dimethylbenzyl)uracil.

Elemental Analysis for C$_{21}$H$_{28}$N$_2$O$_5$ (388.47): Calculated: C, 44.93; H, 7.26; N, 7.21. Found: C, 44.76; H, 7.39; N, 7.11.

This latter compound was then stirred for 34 h in a mixture of triethylamine-methanol-water 1:8:1 (80 ml) at 20° C. to give, after purification by flash column chromatography on silica gel (dichloromethane/methanol 19:1), 0.57 g (76%) of 5-ethyl-1-(3-hydroxypropyloxymethyl)-6-(3,5-dimethyl-benzyl)uracil.

Elemental Analysis for C$_{19}$H$_{26}$N$_2$O$_4$ (346.43): Calculated: C, 65.88; H, 7.56; N, 8.09. Found: C, 65.42; H, 7.46; N, 7.94.

B. Synthesis of 1-(3-N3-hydroxyureidopropyloxymethyl)-6-(3,5-dimethylbenzyl)-5-ethyluracil (Compound No. 1 of the Present Invention)

The 5-ethyl-1-(3-hydroxypropyloxymethyl)-6-(3,5-dimethyl-benzyl)uracil obtained in the above step A (210 mg, 0.6 mmol), phthalimide (110 mg, 0.72 mmol) and triphenylphosphine (0.19 g, 0.72 mmol) were dissolved in tetrahydrofuran and the solution was cooled at 0° C. Then it was added dropwise thereto a solution of isopropyl azodicarboxylate (145 mg, 0.72 mmol) in tetrahydrofuran (2 ml). The reaction medium was then concentrated and subjected to a flash column chromatography on silica gel (dichloromethane/methanol 49:1) and the obtained product was purified by a further flash column chromatography on silica gel (ethyl acetate/petroleum ether 1:1) to give 5-ethyl-6-(3,5-dimethylbenzyl)-1-(3-phthalimidopropyloxymethyl)uracil (0.23 g, 79%).

This latter compound was then subjected to a hydrazinolysis for 2 h under stirring at 20° C. in an ethanolic solution (5 ml) of hydrazine hydrate (240 mg) and purified by chromatography on silica gel (dichloromethane/methanol/ammonia saturated methanol 8:2:0.25) to give 1-(3-aminopropyloxymethyl)-5-ethyl-6-(3,5-dimethylbenzyl)uracil (0.10 g, 59%).

This latter compound (100 mg, 0.29 mmol), in solution in dichloromethane (3 ml), was added to a solution of carbonyldiimidazole (66 mg, 0.41 mmol) in dichloromethane (6 ml) in which was previously added dropwise a solution of O-ter-butyldimethylsilylhydroxylamine (60 mg, 0.41 mmol) in dichloromethane (1 ml) and which was previously stirred for 20 mn at 20° C. After two flash column chromatographies on silica gel (dichloromethane/methanol 19:1), the product was O-desilyled and it was obtained 60 mg (52%) of the desired 1-(3-$N^3$-hydroxyureidopropyloxymethyl)-6-(3,5-dimethylbenzyl)-5-ethyluracil in the form of an oil.

$^1$H-NMR (200 MHz, CDCl$_3$, 40° C.): δ 1.07 (t, 3H, J=7.0 Hz, CH$_2$CH$_3$), 1.82 (quint, 2H, J=6 Hz, CH$_2$—CH$_2$—CH$_2$), 2.30 (s, 6H, Me$_2$Ph), ca 2.5 (s 1, 3H, NH), 2.51 (q, 2H, CH$_2$CH$_3$), 3.40 (t, 2H, NCH$_2$—CH$_2$—CH$_2$—O), 3.70 (t, 2H, OCH$_2$CH$_2$CH$_2$N), 4.09 (s, 2H, CH$_2$Ar), 5.13 (s, 2H, NCH$_2$O), 6.72 (s, 2H, H$_{ortho\text{-}benzyl}$), 6.92 (s, 1H, H$_{para\text{-}benzyl}$).

IR (KBr): $ν_{max}$ 3401($ν_{O\text{-}H}$), 3291, 3186 and 3058($ν_{N\text{-}H}$), 1691($ν_{C=O}$) cm$^{-1}$.

Elemental Analysis for C$_{20}$H$_{28}$N$_4$O$_5$.1/3H$_2$O: Calculated: C, 58.52; H, 7.04; N, 13.65. Found: C, 58.63; H, 6.99; N, 13.44.

Example 5

Synthesis of 1-(3-$N^1$-hydroxyureidopropyloxymethyl)-6-(3,5-dimethylbenzyl)-5-ethyluracil (Compound No. 2 of the Present Invention) (Compound of the Formula I of the present invention in which n=3, $R^1$=ethyl, $R^2$=methyl, $R^3$=OH, $R^4$=H).

To a solution of 5-ethyl-1-(3-hydroxypropyloxymethyl)-6-(3,5-dimethylbenzyl)uracil (prepared as described in the above Example 4-A) (190 mg, 0.548 mmol), of N,O-bis(phenoxycarbonyl)hydroxylamine (165 mg, 0.603 mmol) and of triphenylphosphine (288 mg, 1.09 mmol) in tetrahydrofuran (5 ml), was added dropwise at 0° C. a solution of DIAD (diisopropylazodicarboxylate) (222 mg, 1.09 mmol) in tetrahydrofuran (1 ml). The reaction medium was then brought to 20° C., concentrated, and subjected to a column chromatography on silica gel (ethyl acetate/ether 1:9) and then to a flash column chromatography on silica gel (methanol/chloroform 3:97) to give 250 mg of the intermediate compound 6-(3,5-dimethylbenzyl)-1-[3-(N-phenoxycarbonyl-N-phenoxycarbonyloxyamino)propyloxymethyl]-5-ethyluracil.

This intermediate compound was immediately dissolved in an ammonia saturated methanolic solution (5 ml) and the reaction medium was stirred at 20° C. for 24 h. At this time, the intermediate compound had completely reacted (chromatography on thin layer) and the reaction medium, concentrated, was subjected to a flash column chromatography on silica gel (methanol/ethyl acetate 1:9) to give the desired 1-(3-$N^1$-hydroxypropyloxymethyl)-6-(3,5-dimethylbenzyl)-5-ethyluracil (40 mg, 24%) in the form of a viscous oil which crystallizes spontaneously over several hours at 20° C.

Melting point: 165–167° C.; $R_F$ 0.37 (methanol/ethyl acetate 1:9).

$^1$H-NMR (200 MHz, CD$_3$OD, 40° C.): δ 0.90 (t, 3H, J=7.5 Hz, CH$_2$CH$_3$), 1.85 (quint., 2H, J=6.25 Hz, NCH$_2$CH$_2$CH$_2$O), 2.25 (s, 6H, Me$_2$Ph), 2.40 (q, 2H, CH$_2$CH$_3$), 3.50 (t, 2H, NCH$_2$CH$_2$CH$_2$O), 3.85 (t, 2H, NCH$_2$CH$_2$CH$_2$O), 4.05 (s, 2H, CH$_2$Ph), 5.07 (s, 2H, OCH$_2$N), 6.65 (s el., 2H, H$_{ortho}$-benzyl), 6.85 (s. el., 1H, H$_{para}$-benzyle).

IR (KBr): 3477, 3368 and 3159($ν_{NH}$ and $ν_{OH}$), 1695 and 1650($ν_{C=O}$) cm$^{-1}$. MS (m/z (%)) 359 (1, M$^{\cdot+}$-NH$_2$COH), 341 (7, M$^{\cdot+}$-NH$_2$COH—H$_2$O), 271 (41, M$^{\cdot+}$-NH$_2$CONOH(CH$_2$)$_3$O), 258 (78, M$^{\cdot+}$-NH$_2$CONOH(CH$_2$)$_3$OCH).

Elemental Analysis for C$_{20}$H$_{28}$N$_4$O$_5$.1/3H$_2$O: Calculated: C, 58.52; H, 7.04; N, 13.64. Found: C, 58.55; H, 6.95; N, 13.49.

Example 6

Synthesis of 1-(3-$N^1$-benzoyloxyureidopropyloxymethyl)-6-(3,5-dimethylbenzyl)-5-isopropyluracil (Compound No. 6 of the Present Invention) (Compound of the Formula I of the present invention in which n=3, $R^1$=isopropyl, $R^2$=methyl, $R^3$=benzoyloxy, $R^4$=H).

To a solution of 1-(3-$N^1$-hydroxyureidopropyloxymethyl)-6-(3,5-dimethylbenzyl)-5-isopropyluracil obtained in the above Example 1-C (100 mg, 0.24 mmol) in pyridine (5 ml), was added 30 μl (0.26 mmol) of benzoyl chloride. After 14 hours under stirring at 24° C., the pyridine was eliminated by co-evaporation with toluene (2×10 ml) and the residue was purified by column chromatography on silica gel (petrolcum ether/acetone 3:2) to give 110 mg (88%) of the desired 1-(3-$N^1$-benzoyloxyureidopropyloxymethyl)-6-(3,5-dimethylbenzyl)-5-isopropyluracil in the form of a solid.

Melting point: 160–161° C.; $R_F$ 0.16 (petroleum ether/acetone 3:2).

$^1$H-NMR (200 MHz, CDCl$_3$): δ 1.28 (d, 6H, J=7.0 Hz, CH Me$_2$), 1.92 (quint., 2H, J=6.0 Hz, CH$_2$CH$_2$CH$_2$), 2.30 (s, 6H, Me$_2$Ph), 2.84 (sept., 1H, Me$_2$CH), 3.70 (t, 2H, NCH$_2$CH$_2$CH$_2$O), 3.87 (t, 2H, OCH$_2$CH$_2$CH$_2$N), 4.08 (s, 2H, CH$_2$Ar), 5.10 (s, 2H, NCH$_2$O), 5.22 (s broad, 2H, NH$_2$), 6.70 (s, 2H, H$_{ortho\text{-}benzyl}$), 6.90 (s, 1H, H$_{para\text{-}benzyl}$), 7.52 (dt, 2H, J$_{ortho}$=9.0 Hz, J$_{para}$=0.5 Hz, H$_{meta\text{-}benzoyl}$), 7.70 (dt, 1H, J$_{meta}$=3.5 Hz, H$_{para\text{-}benzoyl}$), 8.10 (dd, 2H, H$_{ortho\text{-}benzoyl}$), 8.98 (s broad, 1H, NH).

IR (KBr): $ν_{max}$ 3431, 3363, 3205($ν_{N\text{-}H}$), 3028–2871($ν_{C\text{-}H}$), 1763 ($ν_{C=O}$ benzoyl), 1680 ($ν_{C=O}$ NC=O) cm$^{-1}$.

MS (m/z (%)) 398 (0.5, M$^{\cdot+}$-OBz), 355 (2, M$^{\cdot+}$-OBz-CONH$_2$), 272 (60, BH$^+$), 257 (100, BH$^+$-Me), 122 (86, OBz), 105 (95, Bz).

Elemental Analysis for C$_{28}$H$_{34}$N$_4$O$_6$.(522.61): Calculated: C, 64.35; H, 6.56; N, 10.72. Found: C, 64.26; H, 6.63; N, 10.56.

Example 7

Synthesis of 1-(2-N1-hydroxyureidoethoxymethyl)-6-(3,5-dimethylbenzyl)-5-ethyluracil (Comparative Compound No. 1)

(Comparative Compound of the Formula I in which n=2, $R^1$=ethyl, $R^2$=methyl, $R^3$=OH, $R^4$=H).

A. Synthesis of 1-(2-acetoxyethoxymethyl)-6-(3,5-dimethylbenzyl)-5-ethyluracil 6-(3,5-dimethylbenzyl)-5-ethyluracil (see the above Example 4-A) (516 mg, 2 mmol) and 1-acetoxy-2-acetoxymethoxyethane [A. Rosowski, S. H. Kim. M. Wick, J. Med. Chem. (1981) 24, 1177–81]) (704 mg, 4 mmol) were suspended, under nitrogen atmosphere, in acetonitrile (20 ml). It was added thereto HMDS (hexamethyldisilazane) (646 mg, 4 mmol) and TMSCl (chlorotrimethyl-silane) (435 mg, 4 mmol) and the mixture was then stirred for 10 mn. Then it was added dropwise thereto, over 10 mn, a solution of tin$^{IV}$ chloride (625 mg, 2.4 mmol) in acetonitrile (5 ml). After 14 h under stirring, it was added thereto dichloromethane (50 ml) and an aqueous saturated sodium hydrogenocarbonate solution (50 ml). The mixture was extracted with dichloromethane (3×50 ml). The organic phases, collected, were washed with a aqueous saturated sodium hydrogenocarbonate solution (25 ml), with water (25 ml), and then with an aqueous saturated sodium chloride solution. The organic phase was dried (sodium sulfate), concentrated, and then subjected to a flash column chromatography (petroleum ether/ethyl acetate 3:2) to give 1-(2-acetoxyethoxymethyl-6-(3,5-dimethylbenzyl)-5-ethyluracil (690 mg, 92%) in the form of a white solid.

Melting point: 126.0–127.0° C. $R_F$ 0.28 (hexane/ethyl acetate 3:2).

1H-NMR (CDCl3, 200 MHz): δ 1.10 (t, 3H, J=7.25 Hz, CH2CH3), 2.08 (s, 3H, Ac), 2.30 (s, 6H, Me$_2$Ph), 2.69 (q, 2H, CH$_2$CH$_3$), 3.80 (m, 2H, AcOCH$_2$CH$_2$O), 4.08 (s, 2H, CH$_2$Ph), 4.20 (m, 2H, AcOCH$_2$), 5.18 (s, 2H, OCH$_2$N), 6.71 (s, 2H, H$_{ortho}$-benzyl), 6.90 (s, 1H, H$_{para}$-benzyl), 8.25 (s el. 1H, NH).

IR (KBr): 3030(νC—H arom.), 2950(νC—H aliphatic), 1740 and 1705 (νC=O) cm−1.

UV (methanol) ν$_{max}$ (ν) 266 nm (8180).

MS (m/z (%)) 374 (4, M$^{·+}$), 255 (16, M$^{·+}$-AcOCH$_2$CH$_2$O), 119 (11, M$^{·+}$-base), 87 (100, AcOCH$_2$CH$_2$$^+$).

Elemental Analysis for $C_{20}H_{26}N_2O_5$ (374.44): Calculated: C, 64.16; H, 7.00; N, 7.48. Found: C, 63.88; H, 7.10; N, 7.37.

B. Synthesis of 6-(3,5-dimethylbenzyl)-5-ethyl-1-(2-hydroxyethoxymethyl)uracil

A solution of 1-(2-acetoxyethoxymethyl)-6-(3,5-dimethylbenzyl)-5-ethyluracil (690 mg, 1.9 mmol) in a mixture of methanol/triethylamine/water 8:1:1 was stirred for 20 hours at 20° C. The solvents were eliminated by evaporation in vacuo and then by co-evaporation with toluene. The obtained solid, recrystallized (methanol), gave 390 mg of 6-(3,5-dimethylbenzyl)-5-ethyl-1-(2-hydroxyethoxymethyl)uracil. The crystallization mother liquors, concentrated, subjected to a flash column chromatography on silica gel (dichloromethane/methanol 19:1) gave a supplemental sample of 80 mg. Total yield: 470 mg (77%) of a white solid.

Melting point: 178.0–179.0° C.; $R_F$ 0.12 (petroleum ether/ethyl acetate 9:1)

$^1$H-NMR (CD$_3$OD, 200 MHz): δ 1.01 (t, 3H, J=7.5 Hz, CH$_2$CH$_3$), 2.25 (s, 6H, Me$_2$Ph), 2.42 (q, 2H, CH$_3$), 3.60 (m, 4H, CH$_2$CH$_2$), 4.12 (s, 2H, CH$_2$Ph), 5.14 (s, 2H, OCH$_2$N), 6.78 (s el. 2H, H$_{ortho}$-benzyl), 6.90 (s el., 1H, H-$_{para}$-benzyl).

IR (KBr): 3380 (ν$_{O-H}$), 3020 (ν$_{C-H}$ arom.), 1708 (ν$_{C=O}$) cm$^{-1}$.

UV (methanol) ν$_{max}$(ν) 207 (41500), 268 (15400).

MS (m/z (%)): 332 (2, M$^{·+}$), 258 (100, B$^+$).

Elemental Analysis for $C_{18}H_{24}N_2O_4$ (332.40): Calculated: C, 65.04; H, 7.28; N, 8.43. Found: C, 64.93; H, 7.30; N, 8.36.

C. Synthesis of 1-(2-N$^1$-hydroxyureidoethoxymethyl)-6-(3,5-dimethylbenzyl)-5-ethyluracil (Comparative Compound No. 1)

To a solution of 6-(3,5-dimethylbenzyl)-5-ethyl-1-(2-hydroxyethoxymethyl)uracil (0.2 g, 0.6 mmol), N,O-bis (phenoxycarbonyl)hydroxylamine (0.18 g, 0.66 mmol) and triphenylphosphine (0.19 g, 0.66 mmol) in tetrahydrofuran (6 ml) was added dropwise at 0° C. DIAD (diisopropylazodicarboxylate) (145 mg, 0.71 mmol). The reaction medium, concentrated, was subjected successively to two flash column chromatographies on silica gel, the first one using a mixture dichloromethane/methanol 49:1 as eluant and the second one, the mixture ethyl acetate/petroleum ether 2:3. It was thus obtained 6-(2,3-dimethylbenzyl)-5-ethyl-1-(2-N,O-bis(phenoxycarbonyl) hydroxyaminoethoxymethyl) uracil (0.30 g, 85%), 0.15 g (0.25 mmol) which was dissolved in a ammonia saturated methanolic solution (10 ml) and stirred for 24 h at 10° C. The reaction medium, concentrated, subjected to a flash column chromatography on silica gel (dichloromethane/methanol 19:1) gave an oil which, taken again with ether, gave the 1-(2-N$^1$-hydroxyureidoethoxymethyl)-6-(3,5-dimethylbenzyl)-5-ethyl-uracil (36.6 mg, 36%) in the form of a white solid.

Melting point: 147–148° C.

$R_F$ 0.18 (dichloromethane/methanol 9:1)

$^1$H-NMR (CDCl$_3$, 200 MHz): δ 1.09 (t, 3H, J=7.5 Hz, CH$_2$CH$_3$), 2.29 (s, 6H, Me$_2$Ph), 2.48 (q, 2H, CH$_2$CH$_3$), 3.22–3.90 (m, 4H, CH$_2$CH$_2$), 4.07 (s, 2H, CH$_2$Ph), 5.10 (s, 2H, OCH$_2$N), 6.70 (s, 2H, H$_{ortho}$-benzyl), 6.90 (s, 1H, H$_{para}$-benzyl), 9.76 (s el., 1H, NH).

IR (KBr): 3498, 3235 and 3190 (νOH and νNH), 1703, 1699 and 1688 (νC=O) cm–1.

MS (m/z (%)) 345 (1, M$^{·+}$NH$_2$CHO), 327 (6, M$^{·+}$-NH$_2$COH—H$_2$O), 271 (100, M$^{·+}$-NH$_2$CONOHCH$_2$CH$_2$O), 258 (73, B$^{30}$ ).

Elemental Analysis for $C_{19}H_{26}N_4O_5$·1/2H$_2$O (339.45): Calculated: C, 57.13; H, 6.81; N, 14.03. Found: C, 56.85; H, 6.63; N, 13.57.

Example 8

Synthesis of 1-(4-N$^1$-hydroxyureidobutyloxymethyl)-6-(3,5-dimethylbenzyl)-5-ethyluracil (Comparative Compound No. 2)

(Comparative Compound of the Formula I in which n=4, R$^1$=ethyl, R$^2$=methyl, R$^3$=OH, R$^4$=H).

A. Synthesis of 4-hydroxybutyl benzoate

To a solution of 1,4-butanediol (18 ml, 0.2 mmol) in pyridine (16 ml), was added slowly at 0° C., under a nitrogen atmosphere, benzoyl chloride (1 ml, 0.1 mmol). After 4 h under stirring at 0° C., the reaction medium was concentrated and the pyridine was eliminated by co-distillation with toluene. The residue was extracted with ether (3×20 ml) and the organic phase was dried (magnesium sulfate), concentrated, and subjected to a flash column chromatography on silica gel (petroleum ether/ethyl acetate 3:2) to give the 4-hydroxybutyl benzoate (9.9 g, 55%) in the form of a colorless oil.

$R_F$ 0.36 (petroleum ether/ethyl acetate 1:1).

$^1$H-NMR (CDCl$_3$, 200 MHz): δ 1.79 (m, 4H, CH$_2$CH$_2$CH$_2$CH$_2$), 3.60 (t, 2H, J=7.0 Hz, CH$_2$OH), 4.34 (t, 2H, J=8.0 Hz, PhCOOCH$_2$), 7.45–8.02 (m, 5H, Ph).

B. Synthesis of 1-(4-benzoyloxybutyloxymethyl)-6-(3,5-dimethylbenzyl)-5-ethyluracil To a solution of 4-hydroxybutyl benzoate (1 g, 5.2 mmol) in dichloromethane (18 ml), was added paraformaldehyde (100 mg, 5.2 mmol). In the mixture, brought at 0° C., was bubbled hydrochloric acid for 2 h. After this time, the vessel was closed and the mixture was stirred at 4° C. for 16 h. The reaction mixture was diluted with dichloromethane (10 ml), dried (magnesium sulfate), and then concentrated. This solution was added to a suspension of 6-(3,5-dimethylbenzyl)5-ethyluracil (obtained as described in the Example 3) (400 mg, 1.55 mmol) and N,O-bis(trimethylsilyl)acetamide (1.1 ml, 4.4 mmol) in dichloromethane (10 ml) previously stirred for 30 mn at 20° C. and then added with tetrabutylammonium iodide (20 mg, 0.05 mmol). The mixture was then heated under reflux for 16 h and then brought to 20° C. Then, the mixture was poured into an aqueous saturated sodium hydrogenocarbonate solution maintained at 0° C. and the mixture was stirred for 30 mn. The organic phase, decanted, was washed with an aqueous saturated sodium chloride solution (15 ml), dried (magnesium sulfate), concentrated and subjected to a flash column chromatography on silica gel (petroleum ether/ethyl acetate 7:3) which gave the 1-(4-benzoyloxybutyloxymethyl)-6-(3,5-dimethylbenzyl)-5-ethyluracile (460 mg, 60%) in the form of an oil.

$R_F$ 0.71 (dichloromethane/methanol 19:1).

$^1$H-NMR (CDCl$_3$, 200 MHz): δ 1.08 (t, 3H, J=8.0 Hz, CH$_2$C$\underline{H}_3$), 1.78 (m, 4H, CH$_2$C$\underline{H}_2$C$\underline{H}_2$CH$_2$), 2.29 (s, 6H, Me$_2$Ph), 2.48 (q, 2H, C$\underline{H}_2$CH$_3$), 3.61 (t, 2H, J=5.5 Hz, (CH$_2$)$_3$C$\underline{H}_2$OCH$_2$), 4.09 (s, 2H, C$\underline{H}_2$Ph), 4.34 (t, 2H, J=6.0 Hz, PhCOOC$\underline{H}_2$), 5.11 (s, 2H, OCH$_2$N), 6.70 (s el., 2H, H$_{ortho}$-benzyl), 6.91 (s, 1H, H$_{para}$-benzyl), 7.40–8.09 (m, 5H, PhCO), 8.38 (s el., 1H, NH).

IR (NaCl): 3050 ($\nu_{C-H}$ arom.), 2924 ($\nu_{C-H}$ aliph), 1702 and 706 ($\nu_{C=O}$) cm$^{-1}$.

UV (EtOH): $\nu_{max}$ (v) 202 (51500), 220 (33300), 267 (15150) nm.

MS (m/z (%)) 464 (1, M$^{\cdot+}$), 270 (58, M$^{\cdot+}$-PhCO$_2$(CH$_2$)$_4$O), 177 (15, PhCO$_2$(CH$_2$)$_4$$^+$), 105 (100, PhCO$^+$).

Elemental Analysis for C$_{27}$H$_{32}$N$_2$O$_5$ (464.57): Calculated: C, 69.81; H, 6.94; N, 6.03. Found: C, 69.66; H, 7.02; N, 5.92.

C. Synthesis of 6-(3,5-dimethylbenzyl)-5-ethyl1-(4-hydroxybutyloxymethyl)-uracil.

1-(4-benzoyloxybutyloxymethyl)-6-(3,5-dimethylbenzyl)-5-ethyluracil (500 mg, 1.08 mmol) was added to a solution of sodium hydroxide (360 mg, 9 mmol) in methanol (50 ml) and the mixture was stirred at 20° C. for 3 h. After neutralization (concentrated hydrochloric acid) and concentration, the residue was subjected to a flash column chromatography (dichloromethane/methanol 19:1) which gave the 6-(3,5-dimethyl benzyl)-5-ethyl-1-(4-hydroxybutyloxymethyl)uracil (190 mg, 48%) in the form of a white solid.

Melting point: 101.4–102.8° C.;

$R_F$ 0.29 (dichloromethane/methanol 19:1).

$^1$H-NMR (CD$_3$OD, 200 MHz): δ 1.00 (t, 3H, J=7.5 Hz, CH$_2$C$\underline{H}_3$), 1.54 (m, 4H, CH$_2$C$\underline{H}_2$C$\underline{H}_2$CH$_2$), 2.26 (s, 6H, Me$_2$Ph), 2.41 (q, 2H, C$\underline{H}_2$CH$_3$), 3.52 (m, 4H, C$\underline{H}_2$CH$_2$CH$_2$C$\underline{H}_2$), 4.11 (s, 2H, C$\underline{H}_2$Ph), 5.10 (s, 2H, OCH$_2$N), 6.75 (s, 2H, H$_{ortho}$-benzyl), 6.90 (s, 1H, H$_{para}$-benzyl).

IR (KBr) 3395 ($\nu_{O-H}$), 1694 and 1637 ($\nu_{C=O}$) cm$^{-1}$.

UV (methanol): $\nu_{max}$ (v) 270 nm (11174).

MS (m/z (%)): 360 (1, M$^{\cdot+}$), 271 (7, M$^{\cdot+}$-O(CH$_2$)$_4$OH), 258 (100, M$^{\cdot+}$-HO(CH$_2$)$_4$OCH$_2$).

Elemental Analysis for C$_{20}$H$_{28}$H$_2$O$_4$ (360.45): Calculated: C, 66.64; H, 7.83; N, 7.77. Found: C, 66.39; H, 7.87; N, 7.63.

D. Synthesis of 1-(4-N$^1$-hydroxyureidobutyloxymethyl)-6-(3,5-dimethylbenzyl)-5-ethyluracil (Comparative Compound No. 2)

To a solution of 6-(3,5-dimethylbenzyl)-5-ethyl-1-(4-hydroxybutyloxymethyl)uracil (180 mg, 0.5 mmol), N,O-bis(phenoxycarbonyl)hydroxylamine (150 mg, 0.55 mmol) and triphenylphosphine (262 mg, 1 mmol) in tetrahydrofuran (5 ml), was added dropwise at 0° C. a solution of DIAD (diisopropylazodicarboxylate) (202 mg, 1 mmol) in tetrahydrofuran (81 ml). The reaction mixture was then brought at 20° C., concentrated and subjected to column chromatography on silica gel (ethyl acetate/ethyl ether 1:9), and then to a flash column chromatography (methanol/chloroform 3:97) to give 260 mg of the intermediate compound 6-(3,5-dimethylbenzyl)-1-[4-(N-phenoxycarbonyl-N-phenoxycarbonyloxyamino)butyloxymethyl]-5-ethyluracil.

This intermediate compound was immediately dissolved in an ammonia saturated methanolic solution (5 ml) and the reaction mixture was stirred at 20° C. for 24 h. At this time, the intermediate compound was completely reacted (chromatography on thin layer) and the reaction mixture, concentrated was subjected to a flash column chromatography on silica gel (methanol/ethyl acetate 1:9) to give the 1-(4-N$^1$-hydroxyureidobutyloxymethyl)6-(3,5-dimethylbenzyl)-5-ethyluracil (45 mg, 23%) in the form of a solid.

Melting point: 148–150° C., $R_F$ 0.40 (methanol/ethyl acetate 1:9).

$^1$H-NMR (CD$_3$OD, 200 MHz): δ 1.00 (t, 3H, J=7.5 Hz, CH$_2$C$\underline{H}_3$), 1.56 (m, 4H, CH$_2$C$\underline{H}_2$C$\underline{H}_2$CH$_2$), 2.25 (s, 6H, Me$_2$Ph), 2.41 (q, 2H, C$\underline{H}_2$CH$_3$), 3.42 and 3.51 (2 t, 2×2H J=6.25 Hz, NC$\underline{H}_2$(CH$_2$)$_2$CH$_2$O and NCH$_2$(CH$_2$)$_2$C$\underline{H}_2$O), 4.11 (s, 2H, C$\underline{H}_2$Ph), 5.10 (s, 2H, OCH$_2$N), 6.72 (s, 2H, H$_{ortho}$-benzyl), 6.90 (s, 1 H, H$_{para}$-benzyl).

IR (KBr): 3485, 3356 and 3158 ($\nu_{NH}$ and $\nu_{OH}$), 1682 and 1652 cm$^{-1}$ ($\nu_{C=O}$).

MS (m/z (%)): 373 (1.5, M$^{\cdot+}$-NH$_2$COH), 355 (20, M$^{\cdot+}$-NH$_2$COH—H$_2$O), 271 (40, M$^{\cdot+}$-NH$_2$CONOH(CH$_2$)$_4$O), 258 (55, BH$^+$), 257 (29, B$^{30}$).

Elemental Analysis for C$_{21}$H$_{30}$N$_4$O$_5$.H$_2$O (436.51): Calculated: C, 59.00; H, 7.30; N, 13.10. Found: C, 59.40; H, 7.28; N, 13.09.

Example 9

Synthesis of 1-(2-N$^1$-hydroxyureidoethoxymethyl)-6-benzyl-5-ethyluracil (Comparative Compound No. 3)

(Comparative Compound of the Formula I in which n=2, R$^1$=ethyl, R$^2$=H, R$^3$=OH, R$^4$=H).

A. Synthesis of 1-(2-acetoxyethoxymethyl)-6-benzyl-5-ethyluracil

To a suspension of 6-benzyl-5ethyluracil (690 mg, 3 mmol), prepared as described in point A of the Example 1 by replacing the 2-bromo-3-methylbutanoic acid by 2-bromobutanoic acid and the 3,5dimethylphenylethanenitrile by phenylethanenitrile, in HMDS (hexamethyldisilazane) (15 ml, 75 mmol), was added under nitrogen atmosphere ammonium sulfate (15 mg). The reaction medium was maintained at ebullition under reflux for 14 h, cooled, and then concentrated in vacuo. The residue was taken again, under nitrogen atmosphere, with anhydrous dichloromethane (12 ml). To the obtained solution were added, under strictly anhydrous conditions, 1-acetoxy-2-acetoxymethoxyethane [A.

Rosowski, S. H. Kim. M. Wick, *J. Med. Chem* (1981) 24, 1177–81] (1.06 g, 6 mmol) and trimethylsilyl triflate (0.57 ml, 3.3 mmol). After 4 h under stirring at 20° C., dichloromethane (12 ml) was added. The organic phase, washed with a saturated sodium hydrogenocarbonate solution (10 ml), and then with a saturated sodium chloride solution (10 ml), dried (magnesium sulfate) and concentrated, was successively subjected to a flash column chromatography on silica gel (chloroform/ethanol 9:1) and then to a second flash column chromatography (petroleum ether/ethyl acetate 1:1) to give the 1-(2-acetoxyethoxymethyl)-6-benzyl-5-ethyluracil (380 mg, 69%) which was immediately subjected to the following step.

B. Synthesis of 6-benzyl-5-ethyl-1-(2-hydroxyethoxymethyl)uracil.

To a solution of 1-(2-acetoxyethoxymethyl)-6-benzyl-5-ethyluracil (1.74 g, 5.02 mmoles in methanol (30 ml) was added a 1 M methanolic solution of sodium methanolate (7 ml). After 14 h under stirring at 20° C., the solution was brought at pH4 with a 1M aqueous solution of hydrochloric acid. The reaction mixture concentrated, subjected to a column chromatography on silica gel (chloroform/ethanol 19:1) gave the 6-benzyl-5-ethyl-1-(2-hydroxyethoxymethyl)uracil (1 g, 66%).

Melting point: 120–122° C., $R_F$ 0.25 (chloroform/ethanol 19:1), $^1$H-NMR (200 MHz, CDCl$_3$): δ 0.88 (t, 3H, J=7.25 Hz, CH$_2$CH$_3$), 2.28 (q, 1H, CH$_2$CH$_3$), 3.42 (m, 4H, CH$_2$CH$_2$), 4.10 (s el., 2H, CH$_2$Ph), 4.65 (t, 1H, J$_{CH2,OH}$=4.5 Hz, CH$_2$OH), 5.01 (s, 2H, OCH$_2$N), 7.25 (s el., 5H, Ph), 11.45 (s el, 1H, NH).

IR (KBr) 3396 ($v_{OH}$), 3028 ($v_{C-H}$ arom.), 2832 ($v_{C-H}$ aliph.) 1706 cm$^{-1}$ ($v_{C=O}$).

Elemental Analysis for C$_{16}$H$_2$ON$_2$O$_4$ (304.35): Calculated: C, 63.14; H, 6.62; N, 9.20. Found: C, 62.94; H, 6.77; N, 9.07.

C. Synthesis of 1-(2-N$^1$-hydroxyureidoethoxymethyl)-6-benzyl-5-ethyluracile (Comparative Compound No. 3)

To a solution of 6-benzyl-5-ethyl-1-(2-hydroxyethoxymethyl)uracil (150 mg, 0.4 mmol) in tetrahydrofuran (3 ml) were added at 20° C. triphenylphosphine (126 mg, 0.48 mmole) and N,O-bis(phenoxycarbonyl) hydroxylamine (120 mg, 0.44 mmol), and then, dropwise, a solution of DIAD (diisopropylazodicarboxylate) (97 mg, 0.48 mmol) in tetrahydrofuran (0.5 ml). The reaction medium, concentrated, was subjected to a flash column chromatography on silica gel (chloroform/ethanol 19:1) to give 300 mg of the intermediated compound 6-benzyl-1-[2-(N-phenoxycarbonyl-N-phenoxycarbonyloxyamino) ethyloxymethyl)-5-ethyluracil, which was immediately dissolved in an ammonia saturated methanolic solution (5 ml). The reaction medium was stirred for 4 h at 20° C., concentrated, and then subjected to a flash column chromatography on silica gel (dichloromethane/ethanol 9:1) to give, after recrystallization (ethyl acetate/methanol), the 1-(2-N$^1$-hydroxyureidoethoxymethyl)-6-benzyl-5-ethyluracil (80 mg, 45%).

Melting point: 276–277° C., $R_F$ 0.25 (dichloromethane/methane 9:1).

$^1$H-NMR (200 MHz, (CD$_3$)$_2$SO, 80° C.): δ 0.89 (t, 3H, J=7.3 Hz, CH$_2$CH$_3$), 2.30 (q, 2H, CH$_2$CH$_3$), 3.47 (t, 2H, J=6.0 Hz, NCH$_2$CH$_2$), 3.59 (t, 2H, CH$_2$CH$_2$O), 4.10 (s el., 2H, CH$_2$Ph), 5.03 (s, 2H, OCH$_2$N), 6.00 (s, 2H, NH$_2$), 7.22 (s el., 5H, Ph), 9.13 (s, 1H, NOH), 11.16(s el., 1H, NH).

IR (KBr): 3475 and 3341 ($v_{NH}$ and $v_{OH}$), 1706 cm$^{-1}$ ($v_{C=O}$).

MS (m/z (%)) 317 (3, M$^{·+}$-NH$_2$COH), 299 (6, M$^{·+}$-NH$_2$COH—H$_2$O), 243 (94, M$^{·+}$-NH$_2$CONOH(CH$_2$)$_2$O), 230 (100, M$^+$-NH$_2$CONOH(CH$_2$)$_2$OCH), UV [MeOH, $v_{max}$ (v)]: 205 (21210), 269 (11200) nm.

Elemental Analysis for C$_{17}$H$_{22}$N$_4$O$_5$ (362.39): Calculated: C, 56.35; H, 6.12; N, 15.46. Found: C, 55.89; H, 6.07; N, 15.20.

What is claimed is:

1. A compound having the following general Formula I:

(I)

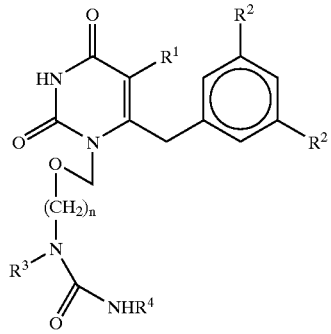

wherein n is equal to 3;

R$^1$ represents an ethyl group or an isopropyl group;

each of the R$^2$ groups represents independently a hydrogen atom, a C$_1$–C$_3$ alkyl group or a halogen atom;

one of the R$^3$ and R$^4$ groups represents a hydrogen atom while the other of the R$^3$ and R$^4$ groups represents an —OH or —OR$^5$ group, wherein R$^5$ may be a C$_2$–C$_7$ acyl group, a C$_{1-C6}$ alkylaminocarbonyl group, an ar(C$_1$–C$_6$)alkylaminocarbonyl group optionally substituted on the aryl, an arylcarbonyl group optionally substituted or a heteroarylaminocarbonyl group, or a pharmaceutically acceptable salt thereof.

2. The compound according to claim 1, wherein R$^1$ represents an isopropyl group.

3. The compound according to claim 1, wherein each R$^2$ represents a methyl group.

4. The compound according to claim 1, wherein R$^3$ represents a —OR$^5$ group and R$^4$ represents a hydrogen atom.

5. The compound according to claim 1, wherein R$^3$ represents a —OH group and R$^4$ represents a hydrogen atom.

6. The compound according to claim 1 wherein R$^5$ represents an acyl group.

7. The compound according to claim 4, wherein R$^5$ represents a pivaloyl group.

8. The compound according to claim 1, which is 1-(3-N$^1$-hydroxyureido-propyloxymethyl)-6-(3,5-dimethylbenzyl)-5-isopropyluracil.

9. The compound according to claim 1, which is 1-(3-N$^1$-acetoxyureido-propyloxymethyl)-6-(3,5-dimethylbenzyl)-5-isopropyluracil.

10. The compound according to claim 1, which is 1-(3-N$^1$-pivaloyloxyureido-propyloxymethyl)-6-(3,5-dimethylbenzyl)-5-isopropyluracil.

11. A process for preparing a compound of the following general Formula I:

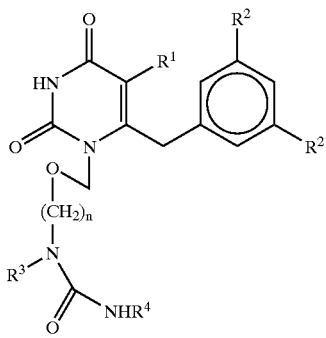

(I)

wherein n is equal to 3;

$R^1$ represents an ethyl group or an isopropyl group;

each of the $R^2$ groups represent independently a hydrogen atom, a $C_1$–$C_3$ alkyl group or a halogen atom;

one of the $R^3$ and $R^4$ groups represents a hydrogen atom while the other of the $R^3$ and $R^4$ groups represents an —OH or —$OR^5$ group, wherein $R^5$ may be an $C_2$–$C_7$ acyl group, a $C_1$–$C_6$ alkylaminocarbonyl group, an ar($C_1$–$C_6$)alkylaminocarbonyl group optionally substituted on the aryl, an arylcarbonyl group optionally substituted or an heteroarylaminocarbonyl group; which comprise the steps of:

a) reacting a compound of the following Formula II:

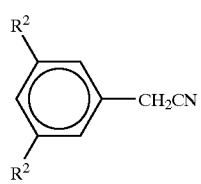

(II)

wherein $R^2$ is as defined above, with a compound of the following Formula III:

$R^1$CHBrCOOEt  (III)

wherein $R^1$ is as defined above, in the presence of Zn, for obtaining a compound of the following Formula IV:

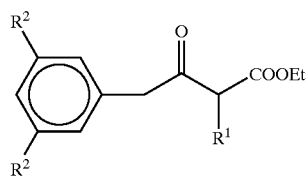

(IV)

wherein $R^1$ and $R^2$ are as defined above;

b) reacting the compound of the Formula IV obtained in the above step a) with thiourea in an basic alcoholic medium for obtaining a thiouracil of the following Formula V:

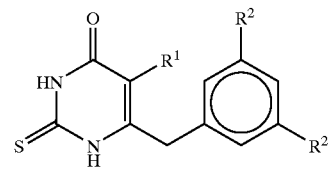

(V)

wherein $R^1$ and $R^2$ are as defined above;

c) reacting the thiouracil of the Formula V obtained in the above step b) with an organic acid for obtaining a compound of the following Formula VI:

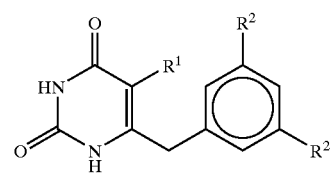

(VI)

wherein $R^1$ and $R^2$ are as defined above;

d) carrying out a glycosidation reaction of the compound of the Formula VI obtained in the above step c) with a compound of the following Formula VII:

MeCOOCH$_2$O(CH$_2$)$_n$OCOMe  (VII)

wherein n is equal to 3, for obtaining an ester, and solvolyzing the ester for providing the alcohol of the following Formula IX:

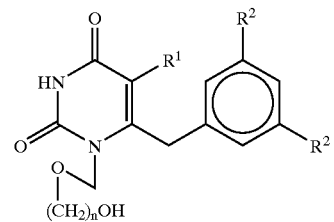

(IX)

wherein n, $R^1$ and $R^2$ are as defined above; and e) subjecting the alcohol of the Formula IX obtained in the above step d) Mitsunobu reaction by using N,O-bis(phenoxycarbonyl)hydroxylamine as a nucleophilic agent for providing a compound of the following Formula X:

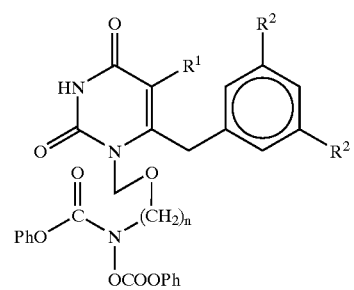

(X)

wherein n, $R^1$ and $R^2$ are as defined above;

f) subjecting the compound of the Formula X obtained in the above step e) to an ammonolysis, for providing the compound of the present invention of the following Formula Ia:

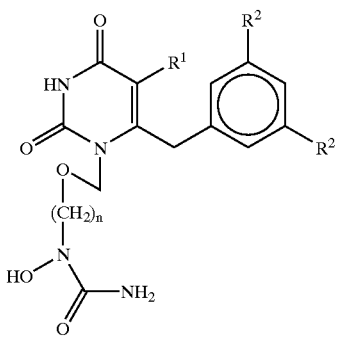
(Ia)

wherein n, $R^1$ and $R^2$ are as defined above; and
g) if required, protecting the —OH group of the compound of the Formula Ia obtained in the above step f) with a $R^5$ group by a O-acylation reaction or by a O-carbamylation reaction for obtaining the compound of the present invention of the following Formula Ib:

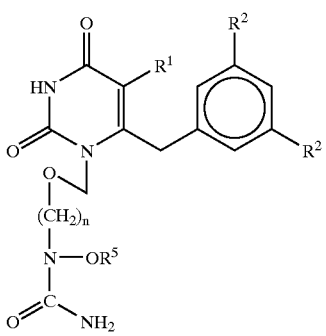
(Ib)

wherein n, $R^1$, $R^2$ and $R^5$ are as defined above;
or
h) subjecting the alcohol of the Formula IX obtained in the above stop c) to a Mitsunobu reaction by using phthalimide as a nucleophilic agent for leading to the amine of the following Formula XI:

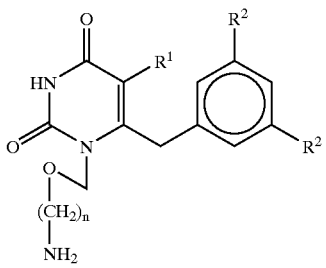
(XI)

wherein n, $R^1$ and $R^2$ are as defined above,
i) treating the amine of the Formula XI obtained in the above step h) with carbonyldiimidazole and O-tertiobutyidimethylsilylhydroxylamine for providing the compound of the following Formula XII:

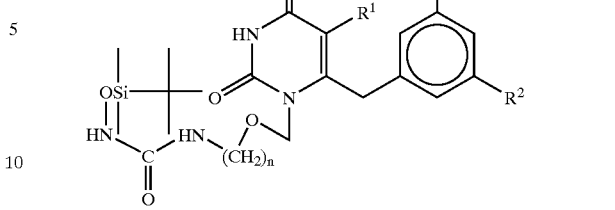
(XII)

wherein n, $R^1$ and $R^2$ are as defined above;
j) desilylating the compound of the Formula XII obtained in the above step i) for obtaining the compound of the following Formula Ic:

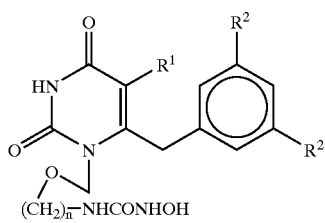
(Ic)

wherein n, $R^1$ and $R^2$ are as defined above;
k) if required, protecting the —OH group of the compound of the Formula Ic obtained in the above step j) with a $R^5$ group by a O-acylation reaction or by a O-carbamylation reaction for obtaining the compound of the following Formula Id:

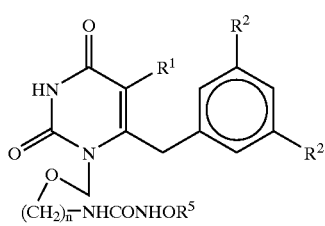
(Id)

wherein n, $R^1$, $R^2$ and $R^5$ are as defined above.

12. A pharmaceutical composition containing at least one compound of claim 1, or its salt in admixture with a pharmaceutically acceptable carrier or excipient.

13. A pharmaceutical composition containing an antiviral efficient amount of a compound of claim 1 or its salt in admixture with a pharmaceutically acceptable carrier or excipient.

14. A process for preparing a medicament which comprises mixing the compound of claim 1 or a pharmaceutically acceptable salt thereof with a pharmaceutically acceptable carrier or excipient.

15. A method of treating AIDS comprising administering an efficient amount of the compound of claim 1 or its salt to a subject from AIDS.

* * * * *